US009163053B2

(12) United States Patent
Siddiqi et al.

(10) Patent No.: US 9,163,053 B2
(45) Date of Patent: *Oct. 20, 2015

(54) NUCLEOTIDE ANALOGS

(75) Inventors: Suhaib Siddiqi, Wakefield, MA (US); J. William Efcavitch, San Carlos, CA (US); Judith Mitchell, Brighton, MA (US); Subramanian Marappan, Acton, MA (US); Jayson Bowers, Cambridge, MA (US); Mirna Jaroza, Arlington, MA (US)

(73) Assignee: Fluidigm Corporation, South San Francisco, CA (US)

( * ) Notice: Subject to any disclaimer, the term of this patent is extended or adjusted under 35 U.S.C. 154(b) by 588 days.

This patent is subject to a terminal disclaimer.

(21) Appl. No.: 12/631,074

(22) Filed: Dec. 4, 2009

(65) Prior Publication Data
US 2011/0081647 A1 Apr. 7, 2011

Related U.S. Application Data

(63) Continuation-in-part of application No. 11/804,591, filed on May 18, 2007, now Pat. No. 7,678,894.

(51) Int. Cl.
C07H 19/00 (2006.01)
C07H 19/04 (2006.01)
C07H 21/02 (2006.01)
C12Q 1/68 (2006.01)
C12P 19/34 (2006.01)
C07H 19/06 (2006.01)
C07H 19/16 (2006.01)
A61K 49/00 (2006.01)

(52) U.S. Cl.
CPC ............... *C07H 19/06* (2013.01); *C07H 19/16* (2013.01); *C12Q 1/6869* (2013.01); *A61K 49/0041* (2013.01); *A61K 49/0052* (2013.01); *C12Q 2563/107* (2013.01)

(58) Field of Classification Search
CPC ........... C12Q 1/6869; C12Q 2563/107; C07H 19/06; C07H 19/16
USPC .................. 536/4.1, 23.1, 26.6; 435/6.1, 91.1
See application file for complete search history.

(56) References Cited

U.S. PATENT DOCUMENTS

| 4,739,044 | A | 4/1988 | Stabinsky |
| 4,757,141 | A | 7/1988 | Fung et al. |
| 6,660,229 | B2 | 12/2003 | Cantor et al. |
| 6,664,079 | B2 | 12/2003 | Ju et al. |
| 7,169,560 | B2 | 1/2007 | Lapidus et al. |
| 7,424,371 | B2 | 9/2008 | Kamentsky |
| 7,476,734 | B2 | 1/2009 | Liu |
| 7,678,894 | B2 * | 3/2010 | Siddiqi ............... 536/23.1 |
| 7,767,805 | B2 | 8/2010 | Buzby |
| 7,956,171 | B2 | 6/2011 | Siddiqi |
| 8,071,755 | B2 | 12/2011 | Efcavitch et al. |
| 8,114,973 | B2 | 2/2012 | Siddiqi et al. |
| 2005/0164182 | A1 | 7/2005 | Pickering et al. |
| 2005/0227231 | A1 | 10/2005 | Tcherkassov |
| 2007/0099222 | A1 | 5/2007 | Gee et al. |
| 2007/0117103 | A1 * | 5/2007 | Buzby ............... 435/6 |
| 2008/0103053 | A1 | 5/2008 | Siddiqi et al. |
| 2008/0227970 | A1 | 9/2008 | Siddiqi et al. |
| 2008/0269476 | A1 | 10/2008 | Siddiqi |
| 2008/0286837 | A1 | 11/2008 | Siddiqi |
| 2009/0061437 | A1 | 3/2009 | Efcavitch et al. |
| 2009/0061439 | A1 | 3/2009 | Buzby |
| 2009/0186351 | A1 | 7/2009 | Siddiqi et al. |
| 2009/0186771 | A1 | 7/2009 | Siddiqi et al. |
| 2010/0203541 | A1 | 8/2010 | Siddiqi |
| 2011/0081647 | A1 | 4/2011 | Siddiqi et al. |
| 2012/0015353 | A1 | 1/2012 | Williams et al. |
| 2012/0040340 | A1 | 2/2012 | Efcavitch et al. |
| 2013/0079232 | A1 | 3/2013 | Kain et al. |
| 2013/0244888 | A1 | 9/2013 | Zhao et al. |

FOREIGN PATENT DOCUMENTS

| JP | H01-213295 A | 8/1989 |
| WO | 01/90417 A2 | 11/2001 |
| WO | 2004/018493 A1 | 3/2004 |
| WO | 2004/024082 A2 | 3/2004 |
| WO | 2006/010084 A2 | 1/2006 |
| WO | 2006/127008 A1 | 11/2006 |
| WO | 2008/144544 A1 | 11/2008 |

OTHER PUBLICATIONS

Agrawal et al., "Site-Specific Functionalization of Oligodeoxynucleotides for Non-Radioactive Labelling," Tetrahedron Letters 31(11): 1543-1546 (1990).
Giusti et al., "Synthesis and Characterization of 5'-Fluorescent-Dye-Labeled Oligonucleotides," PCR Methods and Applications 2(3): 223-227 (1993).
Gupta et al., "A General Method for the Synthesis of 3'-Sulfhydryl and Phosphate Group Containing Oligonucleotides," Nucleic Acids Research 19(11): 3019-3026 (1991).
Holletz et al., "Synthesis and Application of a New Fluorescein Derivative for Fluorescent Labelling of Oligonucleotides and as a Novel Tool for Non-Radioactive DNA Sequencing," Liebigs Annalen der Chemie 1993(10): 1051-1056 (1993).
Huang et al., "Synthesis of Adenosine Derivatives as Transcription Initiators and Preparation of 5' Fluorescein- and Biotin-Labeled RNA through One-Step in Vitro Transcription," RNA 9: 1562-1570 (2003).
Kambara et al., "Optimization of Parameters in a DNA Sequenator using Fluorescence Detection," Nature Biotechnology 6:816-821 (1988).

(Continued)

*Primary Examiner* — Jezia Riley
(74) *Attorney, Agent, or Firm* — Kilpatrick Townsend and Stockton LLP

(57) ABSTRACT

The invention generally relates to nucleotide analogs and methods of their use in sequencing-by-synthesis reactions. In certain embodiments, the invention provides a nucleotide analog including a detectable label attached to a nitrogenous base portion of a nucleotide analog by a cleavable linker, in which contact of the analog with at least one activating agent results in cleavage of the label and elimination of the linker, thereby producing a natural nucleotide, a 9-deaza-G, 9-deaza-A, or ψ-uridine.

38 Claims, 3 Drawing Sheets

(56) References Cited

OTHER PUBLICATIONS

Nelson et al., "Bifunctional Oligonucleotide Probes Synthesized using a Novel CPG Support are Able to Detect Single Base Pair Mutations," Nucleic Acids Research 17(18): 7187-7194 (1989).

Sherrill et al., "Nucleic Acid Analysis using an Expanded Genetic Alphabet to Quench Fluorescence," Journal of the American Chemical Society 126(14): 4550-4556 (2004).

Smith et al., "Fluorescence Detection in Automated DNA Sequence Analysis," Nature 321(6071): 674-679 (1986).

Smith et al., "The Synthesis of Oligonucleotides Containing an Aliphatic Amino Group at the 5' Terminus: Synthesis of Fluorescent DNA Primers for Use in DNA Sequence Analysis," Nucleic Acids Research 13(7): 2399-2412 (1985).

Sproat et al., "The Synthesis of Protected 5'-Mercapto-2',5'-Dideoxyribonucleoside-3'-0-hosphorainidites; Uses of 5'-Mercapto-Oligodeoxyribonucleotides," Nucleic Acids Research 15(12): 4837-4848 (1987).

Zofall et al, "Two Novel dATP Analogs for DNA Photoaffinity Labeling," Nucleic Acids Research 28(21); 4382-4390 (2000).

Zuckermann et al., "Efficient Methods for Attachment of Thiol Specific Probes to the 3'-Ends of Synthetic Oligodeoxyribonucleotides," Nucleic Acids Research 15(13): 5305-5321 (1987).

International Search Report for PCT Application No. PCT/US2008/063945 mailed Aug. 26, 2008.

Wu et al., "3'-O-modified nucleotides as reversible terminators for pyrosequencing", PNAS, vol. 104, No. 42, Oct. 16, 2007, pp. 16462-16467.

Seo et al., "Photocleavable fluorescent nucleotides for DNA sequencing on a chip constructed by site-specific coupling chemistry", PNAS, vol. 101, No. 15, Apr. 13, 2004, pp. 5488-5493.

\* cited by examiner

NUCLEOTIDE ANALOGS

RELATED APPLICATIONS

This application is a continuation-in-part of U.S. patent application Ser. No. 11/804,591, filed May 18, 2007, the contents of which are incorporated by reference herein in its entirety.

FIELD OF THE INVENTION

The invention generally relates to nucleotide analogs and methods of their use in sequencing-by-synthesis reactions.

BACKGROUND

Single molecule sequencing is used to obtain high-throughput sequence information on individual DNA or RNA. See, Braslaysky, Proc. Natl. Acad. Sci. USA 100: 3960-64 (2003). Sequencing-by-synthesis involves template-dependent addition of nucleotides to a template/primer duplex. Nucleotide addition is mediated by a polymerase enzyme and nucleotides may be labeled in order to facilitate their detection. All four Watson-Crick nucleotides may be added simultaneously, each with a different detectable label or nucleotides may be added one at a time in a step-and-repeat manner for imaging incorporation.

A challenge that has arisen in single molecule sequencing involves the ability to sequence through homopolymer regions (i.e., portions of the template that contain consecutive identical nucleotides). Often the number of bases present in a homopolymer region is important from the point of view of genetic function. As most polymerases used in sequencing-by-synthesis reactions are highly-processive, they tend to add bases continuously as the polymerase traverses a homopolymer region. Detectable labels used in sequencing generally have not been able to be resolved over multiple consecutive incorporations.

Some approaches have been devised that are intended to address the problem encountered with a highly-processive polymerase, but these approaches result in a nucleotide that is "scarred" upon release of inhibition. These "scarred" nucleotides often serve as poor substrates for the polymerase enzyme, making subsequent incorporations difficult. Thus, there is a tension between the desire to achieve step-and-repeat nucleotide incorporation and the desire for a highly-processive polymerase that will easily incorporate nucleotide analogs.

There is a need for detectably labeled nucleotides that do not hinder or inhibit ability of a polymerase to incorporate subsequent detectably labeled nucleotides into a nascent strand of DNA or RNA.

SUMMARY

The invention generally relates to nucleotide analogs that have a detectable label attached via a cleavable linker. The cleavage of the linker after incorporation into a primer-template duplex, results in a native (i.e., scarless) or an essentially native (i.e., capless, or post-incorporation modified) nucleotide. Because the nucleotides analogs of the invention revert to natural or essentially native nucleotides after incorporation and cleavage events, the nucleotide analogs of the invention do not hinder or inhibit ability of a polymerase to incorporate subsequent detectably labeled nucleotides into a nascent strand of DNA or RNA. Accordingly, sequencing reactions are conducted with altered nucleotides designed to limit polymerase-mediated processivity. As a result, one is able to conduct a sequencing-by-synthesis reaction that allows incorporation of a single nucleotide for imaging prior to unhindered incorporation of subsequent nucleotides into the primer.

Generally, embodiments of the invention are represented by molecules of the following type:

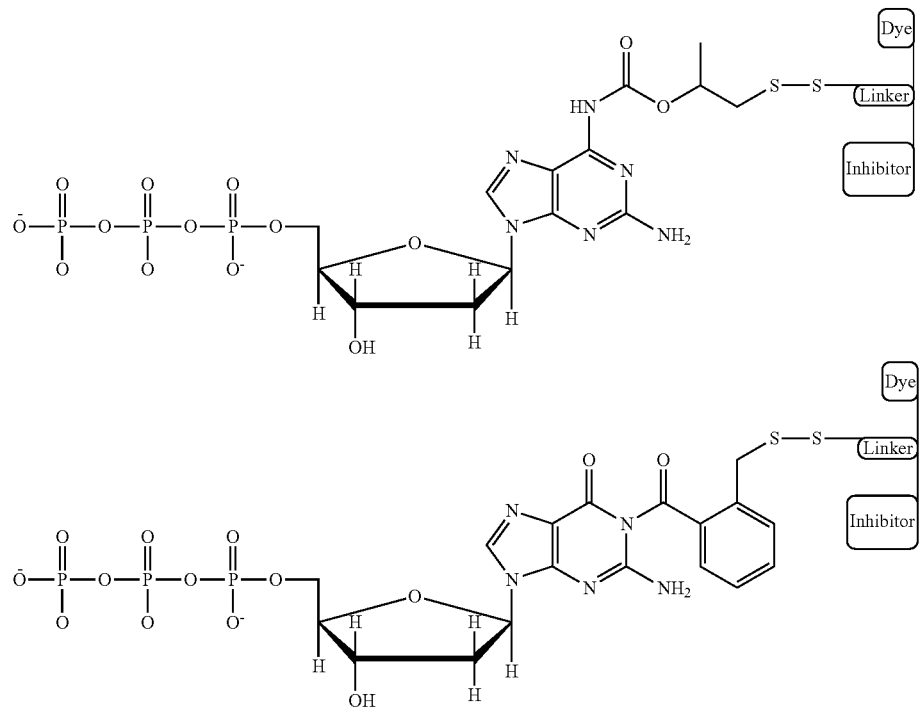

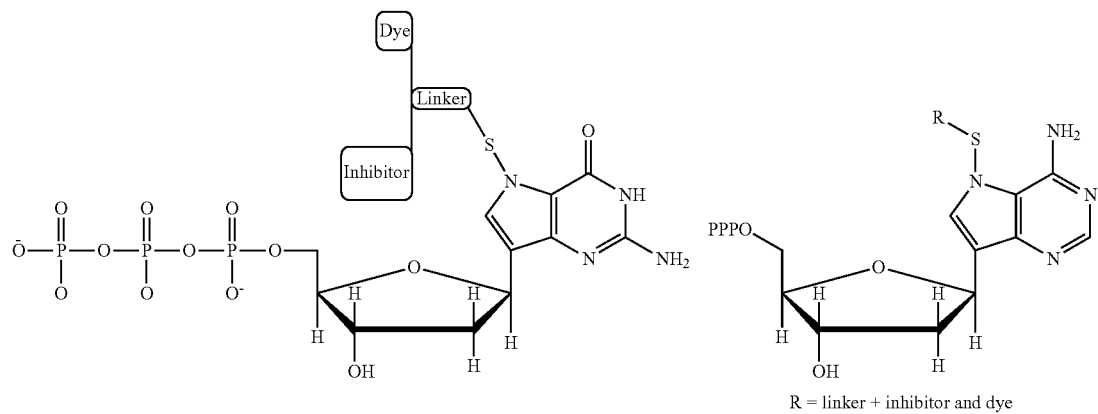
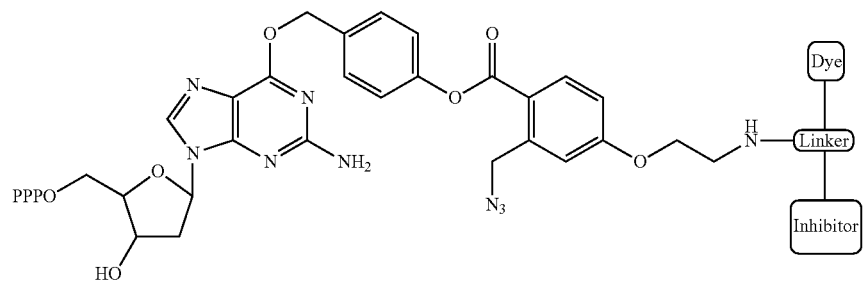
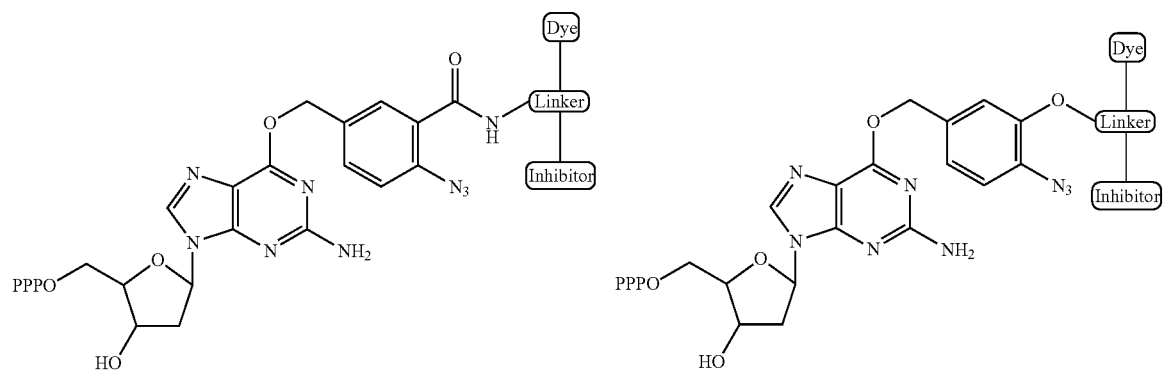
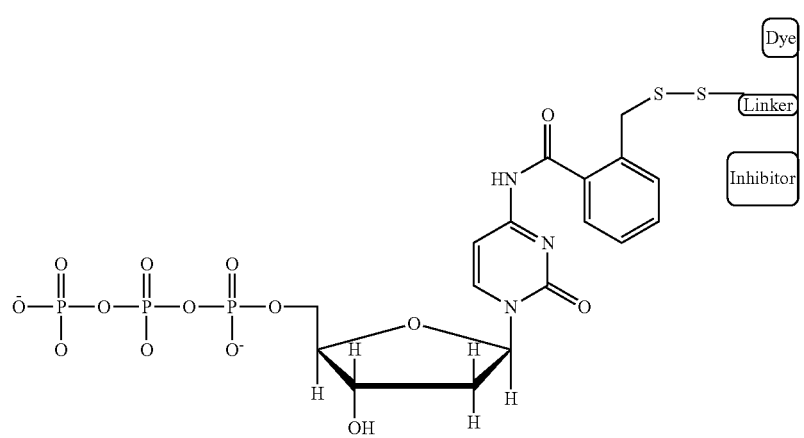

-continued

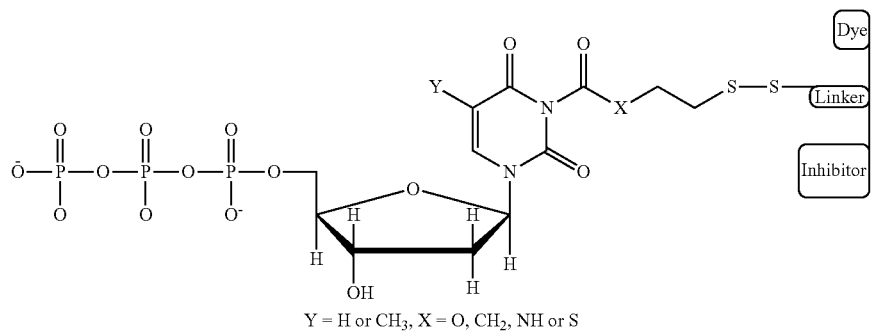

Y = H or CH₃, X = O, CH₂, NH or S

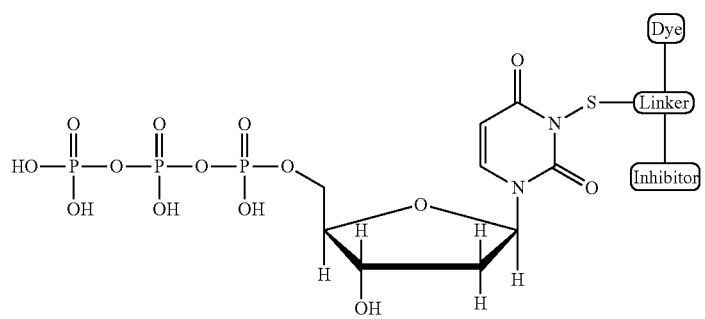

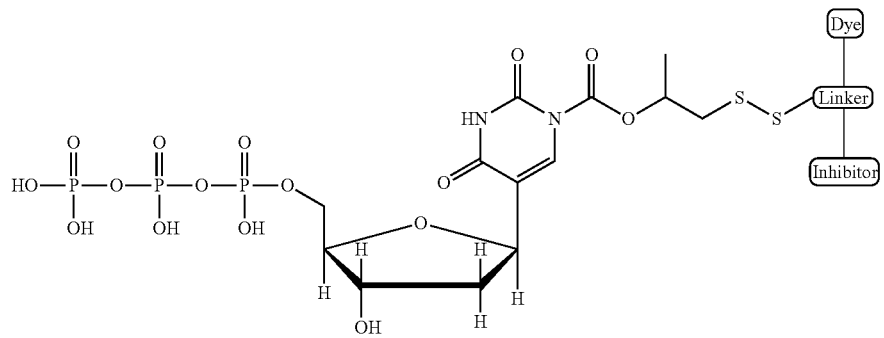

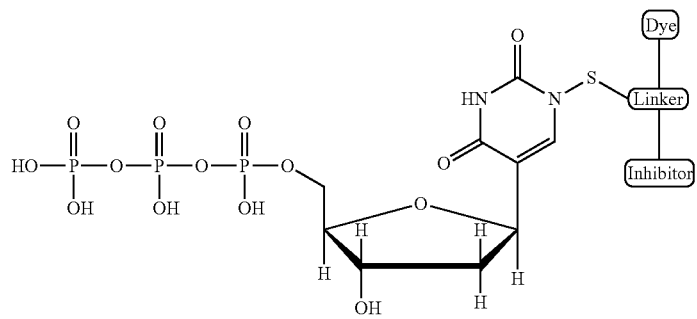

An aspect of the invention provides a nucleotide analog including a detectable label attached to a nitrogenous base portion of a nucleotide analog by a cleavable linker, in which contact of the analog after enzymatic incorporation with at least one activating agent results in cleavage of the label and elimination of the linker, thereby producing a natural nucleotide or a scarless 2'-deoxy-9-deaza-guanine ("scarless 9-deaza-G") or a scarless 2'deoxy-9-deaza-adenine ("scarless 9-deaza-A") or a scarless 2'-deoxy-ψ-uridine ("scarless ψ-uridine"). Exemplary nucleotide analogs of the invention that revert to scarless nucleotides after cleavage of the label include:

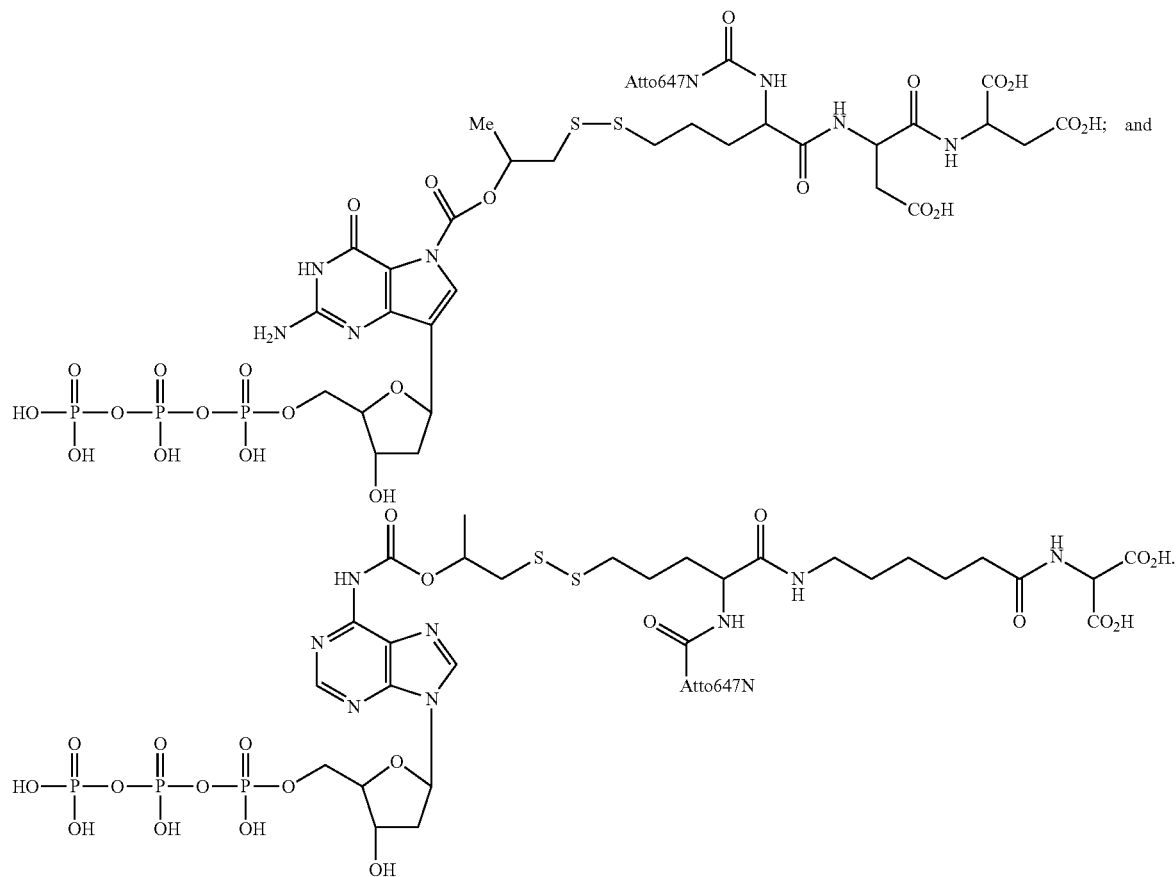

Cleavage of the label is induced by contact of the nucleotide analogs with an activating agent. The activating agent for cleavage may be a chemical agent as with respect to the above molecules, or light such as when the portions of the preceding molecules between the nitrogenous base and the S—S functionality are replaced with any of a variety of known photo-cleavable moieties. Exemplary chemical agents include reducing agents such as TCEP, THP, DTT, THPP, cysteine or glutathione or combinations thereof.

The linker may include any type of chemistry that upon contact with the activating agent or agents results in cleavage of the linker to release the detectable label and also results in elimination of any portion of the linker that remains attached to the nucleotide analog after a cleavage of the label, thereby producing a nucleotide that is recognized by a polymerase as natural. An exemplary linker is a linker that includes a disulfide bond. Additional linkers that may be used are Staudinger linkers. In certain embodiments, a cyclization reaction is used to eliminate the portion of the linker that remains attached to the nucleotide analog after cleavage. Non-limiting examples of cyclization reactions are shown below. Other elimination mechanisms such as photochemically or free radical mediated reactions can be used.

Nucleotide analogs of the invention are designed such that the cleavable linker is attached to the nitrogenous base portion of the analog. For example, the linker may be attached to N3 of the base when the base is thymine or uracil, attached to N4 of the base when the base is cytosine or adenine, attached to N1, N2, or O6 of the base when the base is guanine, attached to N5 of the base when the base is ψ-uridine or attached to N7 of the base when the base is 9-deaza-G or 9-deaza-A.

Any detectable label may be used with nucleotide analogs of the invention, such as fluorescent labels, radiolabels, enzymatic labels, and others. In particular embodiments, the detectable label is an optically-detectable label, such as a fluorescent label. Exemplary fluorescent labels include Atto, cyanine, rhodamine, fluorescien, coumarin, BODIPY, alexa, and conjugated multi-dyes.

Another aspect of the invention provides a nucleotide analog including a detectable label attached to a nitrogenous base portion of a nucleotide analog by a cleavable linker, in which contact of the analog with at least one activating agent results in cleavage of the label and a first portion of the linker, in which a second portion of the linker that remains attached to the analog is neutral in charge. In certain embodiments, the second portion of the linker does not contain either an oxygen atom or a nitrogen atom. As illustrated by particular implementations represented in FIGS. 3 and 4, an oxygen or nitrogen atom in the second portion has the effect of reducing the initial incorporation rate (e.g., compare dC-cap or dG Acetamide Cap with the other structures). For convenience, the term "neutral in charge" may hereafter generally be understood to include those embodiments in which the second portion of the linker does not contain either an oxygen atom or a nitrogen atom.

The linker may include a chemistry such that after cleavage of the label and the first portion of the linker, the second portion of the linker does not require any subsequent chemical modification to render it neutral in charge (a "capless nucleotide"). Alternatively, the linker may include a chemistry such that after cleavage of the label and the first portion of the linker, the second portion of the linker undergoes a subsequent chemical modification, rendering the second portion of the linker neutral in charge (a "post-incorporation modified nucleotide"). A linker having chemistry that produces a capless nucleotide or a linker having chemistry that produces a post-incorporation modified nucleotide ultimately produce the same type of nucleotide analog, i.e., a nucleotide analog in which a portion of the linker that remains attached to the nucleotide is neutral in charge. Thus capless and post-incorporation modified nucleotides of the invention impart the same advantages for sequencing reactions, i.e., the rate or extent of the sequencing reaction is not diminished after many rounds of polymerase-mediated addition of detectably labeled nucleotides to the nascent strand of DNA or RNA. In certain embodiments, the first portion of the linker includes a carbamate group.

Exemplary nucleotide analogs of the invention that upon cleavage of the label generate a capless or post-incorporation modified nucleotide include:

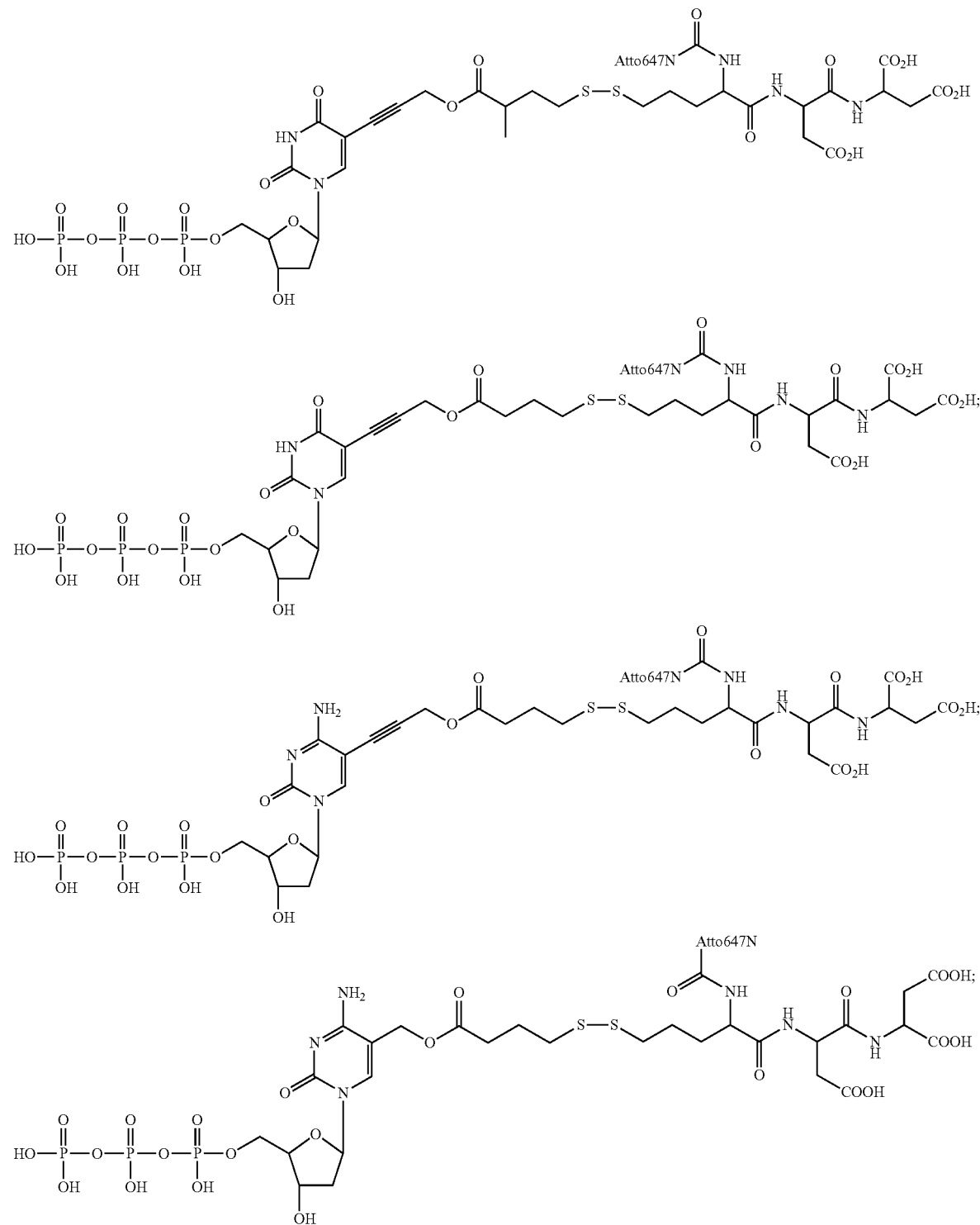

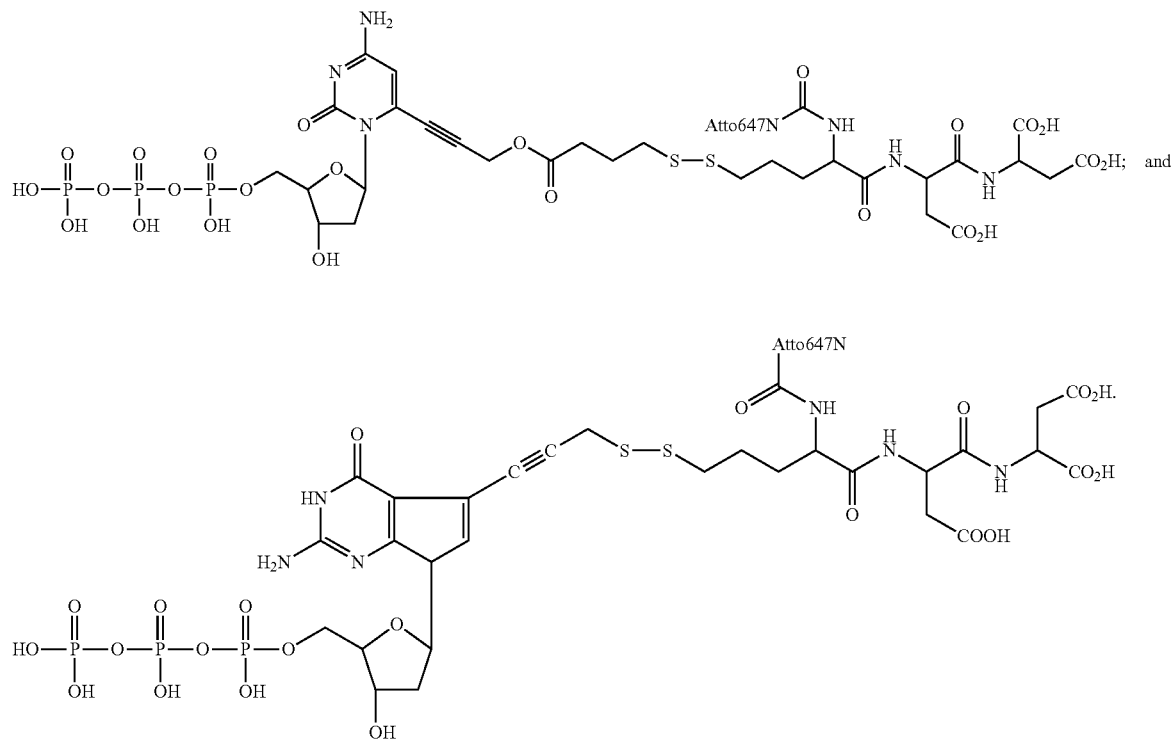

Examples of "Cap" include:

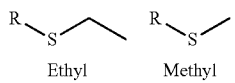

Ethyl     Methyl

Another aspect of the invention includes a method of sequencing a nucleic acid including directly or indirectly anchoring a nucleic acid duplex to a surface, the duplex including a template portion and a primer portion hybridized thereto, exposing the duplex to a nucleotide analog of the invention in the presence of a polymerase capable of catalyzing the addition of the nucleotide analog to the primer portion in a template-dependent manner, detecting incorporation of the nucleotide analog into the primer portion, contacting the nucleic acid duplex with an activating agent, thereby cleaving the detectable label and eliminating the linker to produce a natural nucleotide, a scarless 9-deaza-G, a scarless 9-deaza-A, a scarless 9-deaza-A, or a ψ-uridine, and repeating the exposing, detecting, and contacting steps at least once.

Another aspect of the invention provides a method of sequencing a nucleic acid including directly or indirectly anchoring a nucleic acid duplex to a surface, the duplex comprising a template portion and a primer portion hybridized thereto, exposing the duplex to a nucleotide analog of the invention in the presence of a polymerase capable of catalyzing the addition of the nucleotide analog to the primer portion in a template-dependent manner, detecting incorporation of the nucleotide analog into the primer portion, contacting the nucleic acid duplex with an activating agent, thereby cleaving the detectable label and a first portion of the linker, and producing a nucleotide analog in which a second portion of the linker that remains attached to the analog and is neutral in charge (but, in these illustrative embodiments, also including O or N atoms), and repeating the exposing, detecting, and contacting steps at least once.

Yet another aspect of the invention provides a method of sequencing a nucleic acid including directly or indirectly anchoring a nucleic acid duplex to a surface, the duplex comprising a template portion and a primer portion hybridized thereto, exposing the duplex to a nucleotide analog of the invention in the presence of a polymerase capable of catalyzing the addition of the nucleotide analog to the primer portion in a template-dependent manner, detecting incorporation of the nucleotide analog into the primer portion, contacting the nucleic acid duplex with an activating agent, thereby cleaving the detectable label and a first portion of the linker, and producing a nucleotide analog in which a second portion of the linker that remains attached to the analog and is neutral in charge (but, in these illustrative embodiments, not including O or N atoms), and repeating the exposing, detecting, and contacting steps at least once.

Methods of the invention can further include removing unincorporated nucleotide analog and polymerase in all or some repetitions of the exposing, detecting, and contacting steps.

Analogs of the invention are reversible inhibitors or blockers that allow the incorporation of only one nucleotide per addition cycle in a template-dependent sequencing-by-synthesis reaction. The compositions described herein are useful in any sequencing reaction, but are especially useful in single molecule sequencing-by-synthesis reactions. Single molecule reactions are those in which the duplex to which nucleotides are added is individually optically resolvable.

The nitrogenous base portion of the nucleotide is selected from the standard Watson-Crick bases and their analogs and variants or analogs. In a specific embodiment, the invention provides a nucleotide analog comprising a nucleotide to be incorporated linked to a blocking nucleotide comprising a traditional Watson-Crick base (adenine, guanine, cytosine, thymidine, or uridine), a sugar for example, a ribose or deoxy ribose sugar, and at least one phosphate.

The invention also provides methods for sequencing nucleic acids. In certain methods, a nucleic acid duplex, comprising a template and a primer, is positioned on a surface such that the duplex is individually optically resolvable. A sequencing-by-synthesis reaction is performed under conditions to permit addition of the labeled nucleotide analog to the primer while preventing another nucleotide or nucleotide analog from being added immediately downstream. After incorporation has been detected, inhibition is removed to permit another nucleotide to be added to the primer. Methods of the invention allow, among other things, detection and counting of consecutive nucleotides in a template homopolymer region.

DETAILED DESCRIPTION

Figure 1:
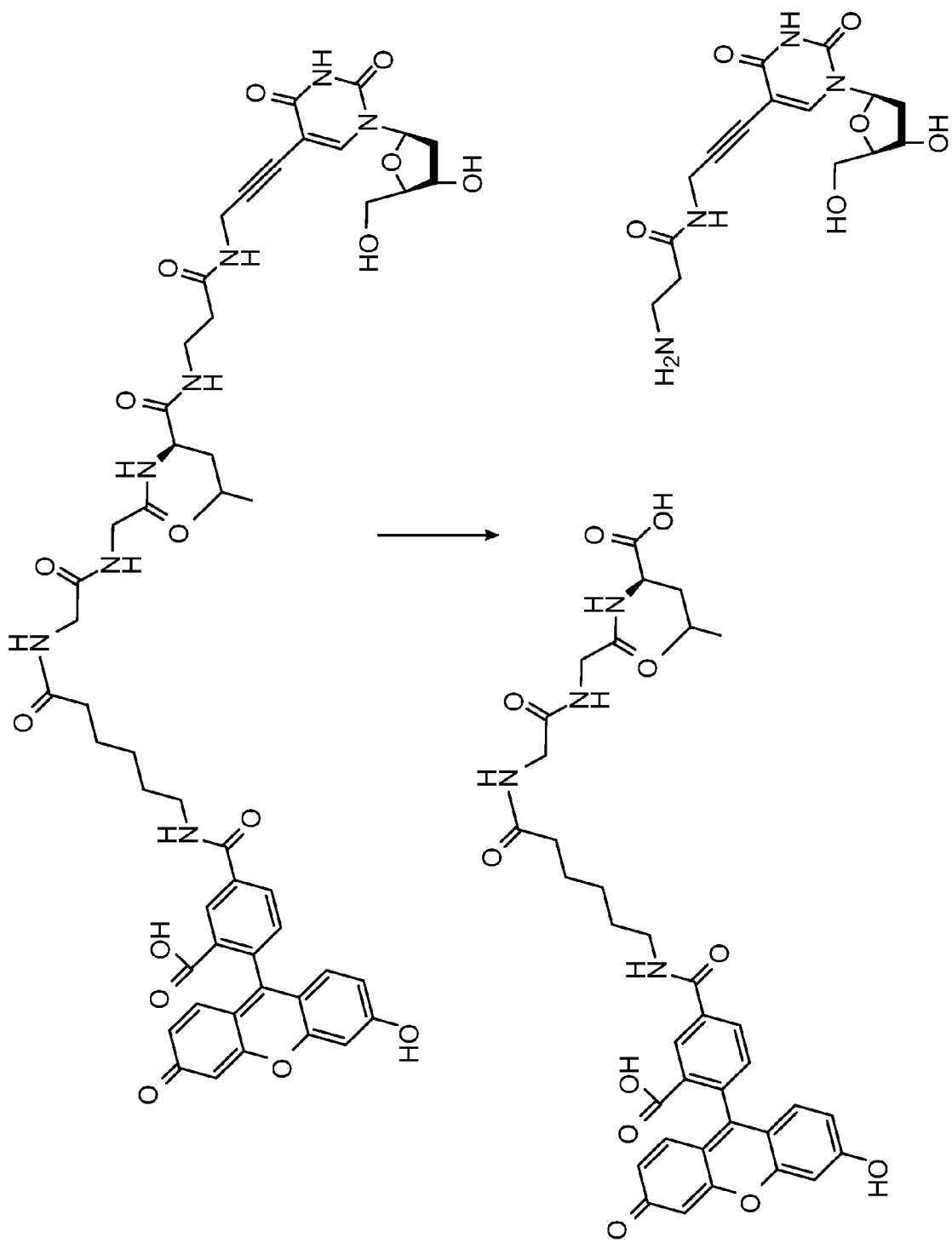
FIG. 1 is a diagram showing a prior art nucleotide analog having a reporter moiety linked to the nucleotide analog. The scheme further shows the nucleotide analog after cleavage of the linker.

Prior art nucleotide analogs of the invention have used linkers to attach blocking moieties and/or reporter moieties to the nucleotide analog. Blocking moieties help control processivity of a polymerase while reporter moieties are used for imaging a nucleotide once it has been incorporated into a nascent strand of DNA or RNA. Sometimes a single chemical moiety can act as the blocking moiety and the reporter moiety. A top portion of FIG. 1 shows an exemplary prior art nucleotide analog having a linker that couples a chemical moiety that acts as both a reporter moiety and a blocking moiety. A problem with these prior art nucleotide analogs is that upon cleavage of the blocker/reporter moiety, the incorporated nucleotide is left with an overhang or a "scar", i.e., a certain number of atoms of the linker remain attached to the nucleotide analog. The lower portion of the schematic of FIG. 1 shows a prior art nucleotide after the blocker/reporter has been cleaved. The chemical moiety remaining attached to the nitrogenous base portion of the nucleotide is the scar. These "scarred" nucleotides serve as poor substrates for the polymerase enzyme, making subsequent incorporations difficult or impossible.

The invention provides nucleotide analogs that are useful in sequencing-by-synthesis reactions. The analogs of the invention include a detectable label attached to the analog by a cleavable linker. The cleavable linkers include a chemistry that upon cleavage of the linker results in native nucleotides (i.e., scarless) or essentially native nucleotides (i.e., capless or post-incorporation modified). Because the nucleotide analogs of the invention revert to native nucleotides (i.e., scarless) or essentially native nucleotides (i.e., capless or post-incorporation modified) after incorporation and cleavage events, the nucleotide analogs of the invention do not hinder or inhibit ability of a polymerase to incorporate subsequent detectably labeled nucleotides into a nascent strand of DNA or RNA.

Analogs of the invention are based upon any of the standard Watson-Crick nucleotides (i.e., A, G, C, T, or U) or their variants, and may be in the mono-, di-, tri-, or bis phosphate configuration. The analogs may contain traditional ribose or deoxyribose sugar groups or non-traditional groups such as an acyNTP construct and others known to those skilled in the art.

A linker refers to a chemical entity that serves to connect a detectable label or a blocking moiety with any portion of a nucleotide. In certain embodiments, the linker is connected to a nitrogenous base portion of the nucleotide analog. The linker may be connected to any atom on of the nitrogenous base portion of the nucleotide analog. For example, the linker may be attached to N3 of the base when the base is thymine or uracil, attached to N4 of the base when the base is cytosine or adenine, attached to N1, N2, or O6 of the base when the base is guanine, attached to N5 when the base is ψ-uridine or attached to N7 of the base when the base is 9-deaza-G or 9-deaza-A.

The linker may include any type of chemistry that upon contact with an activating agent results in cleavage of the linker to release the detectable label and also results in elimination of any portion of the linker that remains attached to the nucleotide analog, thereby producing the natural nucleotide. An exemplary linker is a linker that includes a disulfide bond. Additional linkers that may be used are Staudinger linkers. In certain embodiments, a cyclization reaction is used to eliminate the portion of the linker that remains attached to the nucleotide analog after cleavage. The resulting nucleotide advantageously is a native nucleotide. This allows highly efficient subsequent nucleotide incorporation into a nascent strand of DNA or RNA in a sequencing by synthesis reaction.

An exemplary set of four detectable dNTP analogs includes N6-substituted dATP, N7-substituted-9-deaza dGTP, N4-substituted dCTP, and C5-substituted dUTP. A nascent strand of DNA or RNA is produced upon incorporation of those analogs. Exemplary structures of nucleotide analogs of the invention that produce natural nucleotides upon incorporation into a nascent strand of DNA or RNA and after cleavage of the detectable label include:

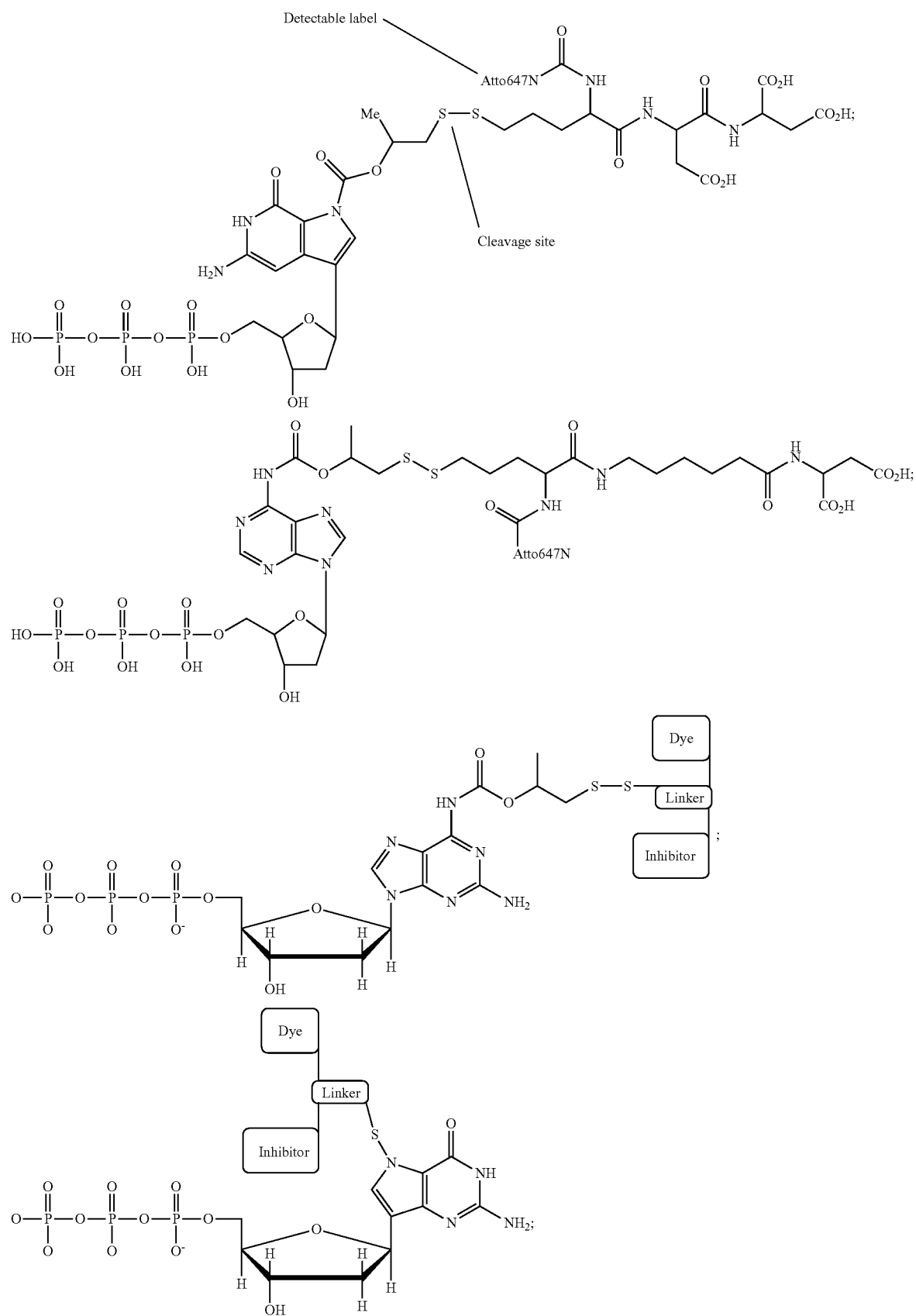

-continued
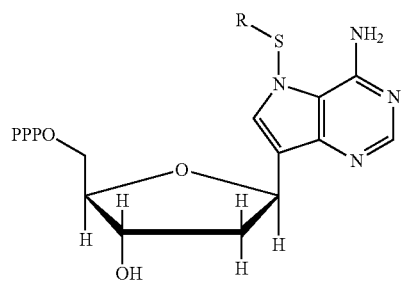
R = linker + inhibitor and dye
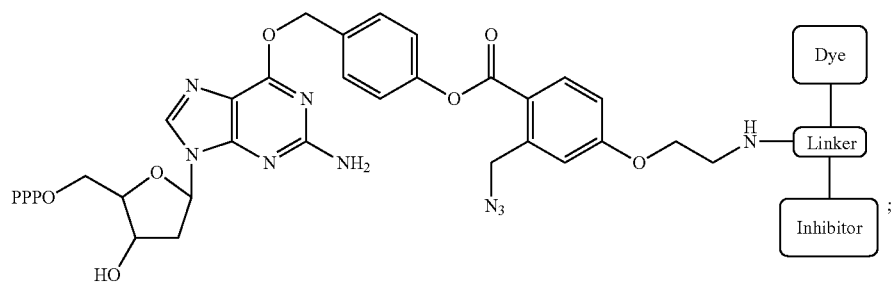
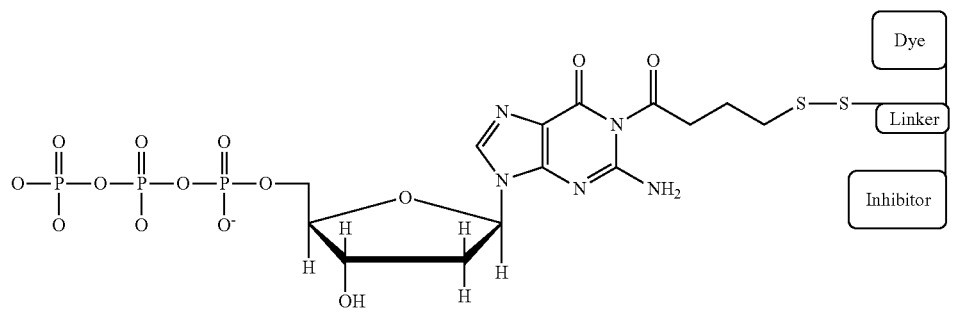
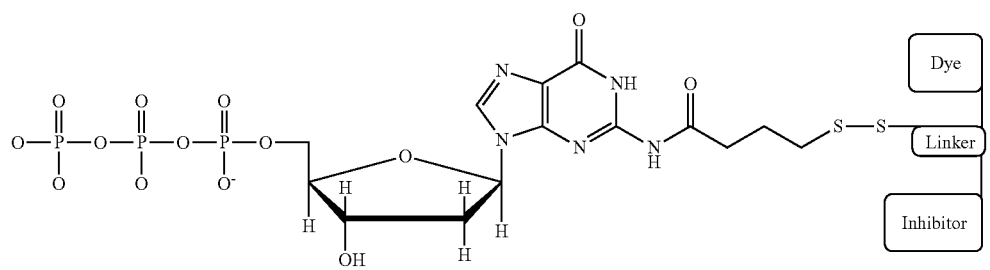
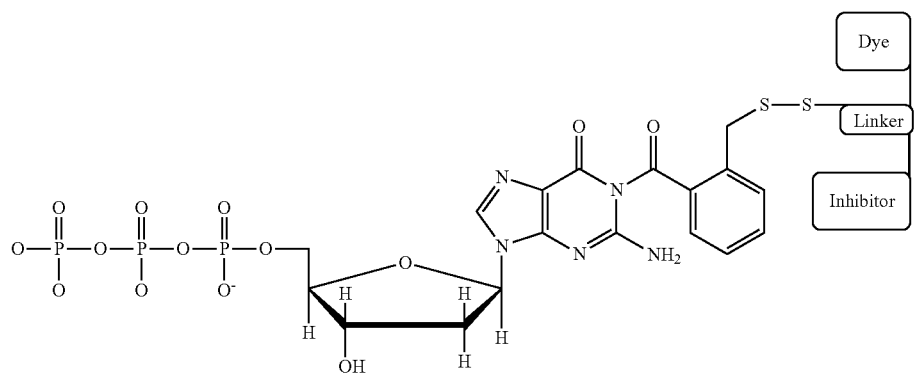

-continued
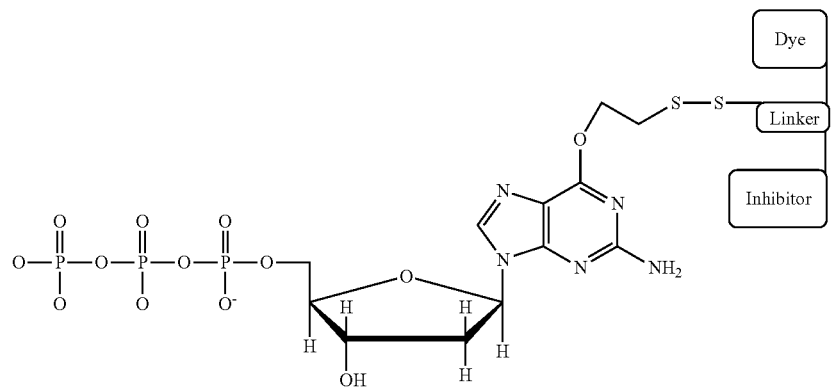
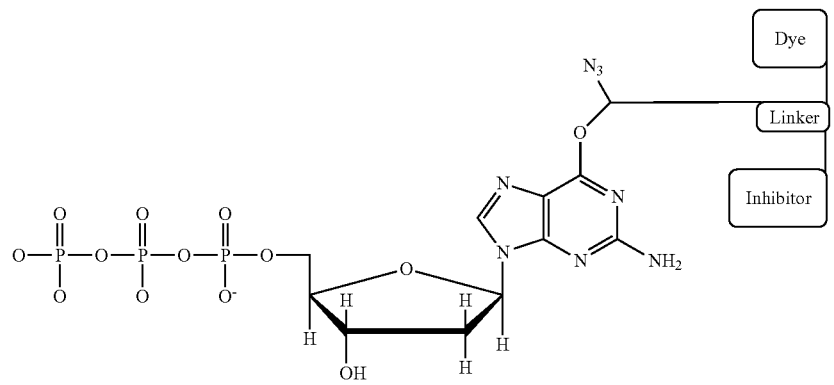
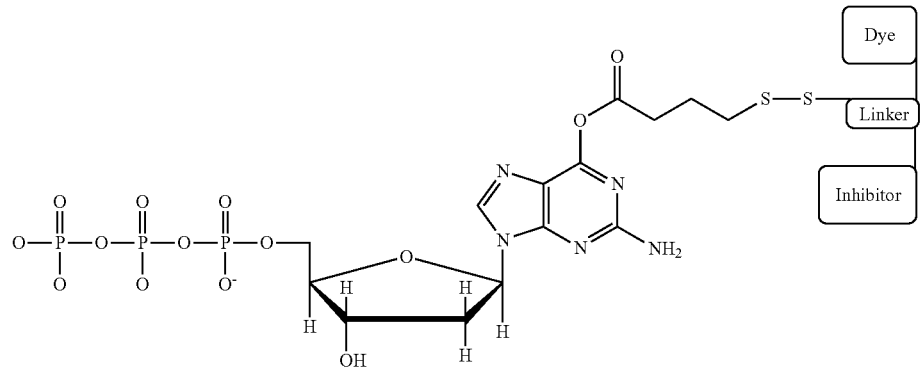
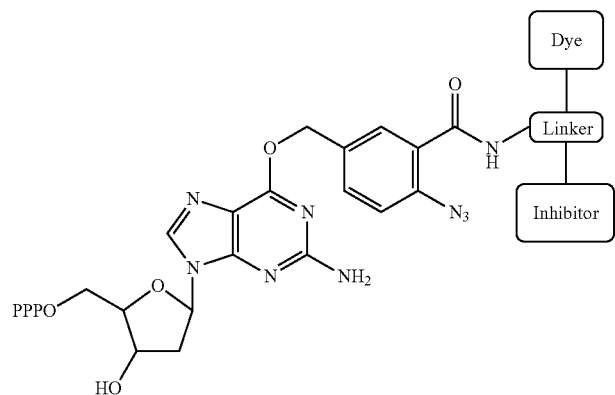

-continued
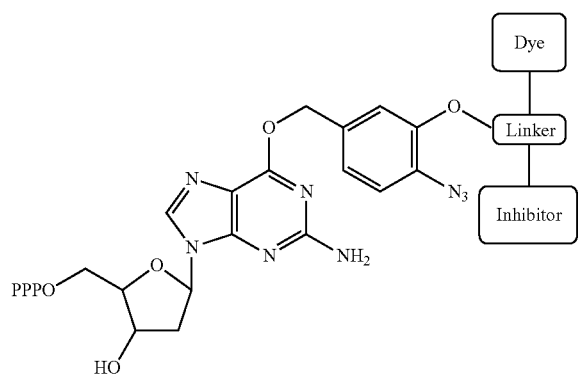
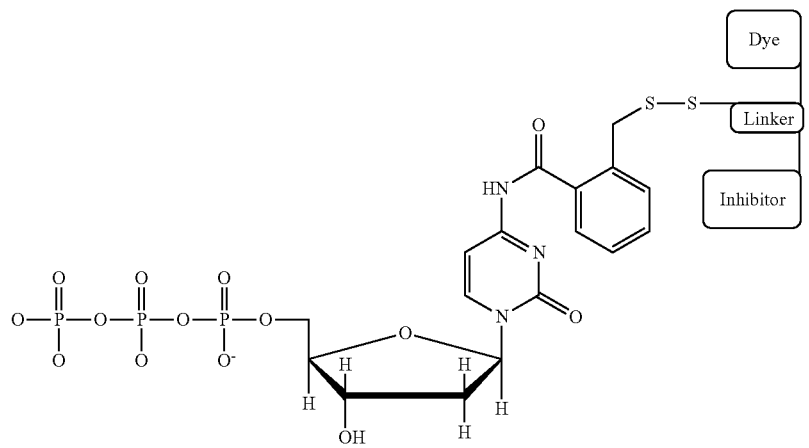
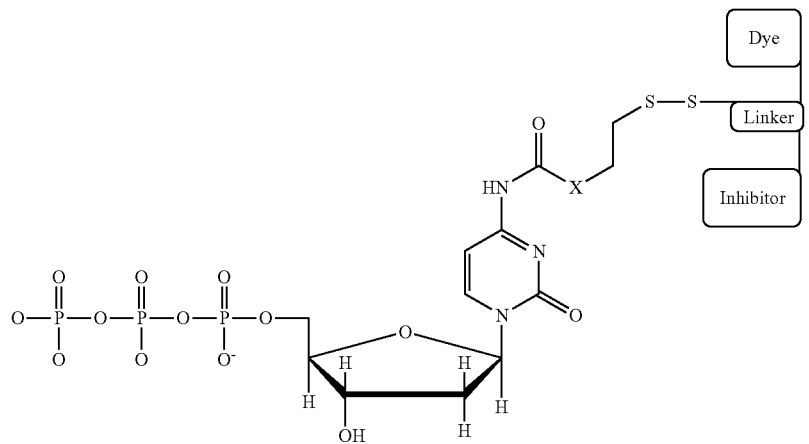
X = O, NH, S, CH₂
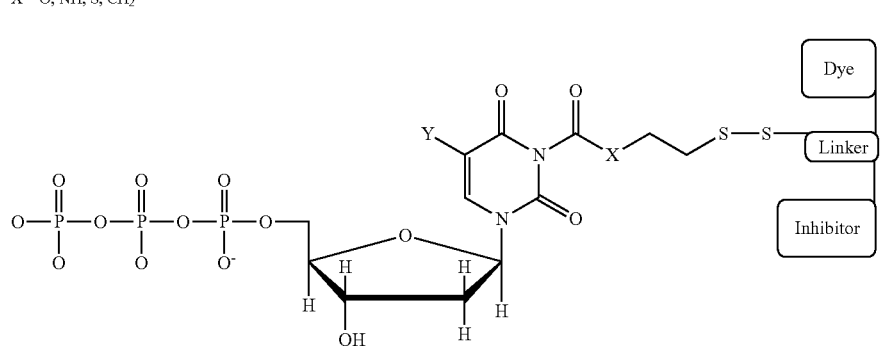
Y = H or CH₃, X = O, CH₂, NH or S

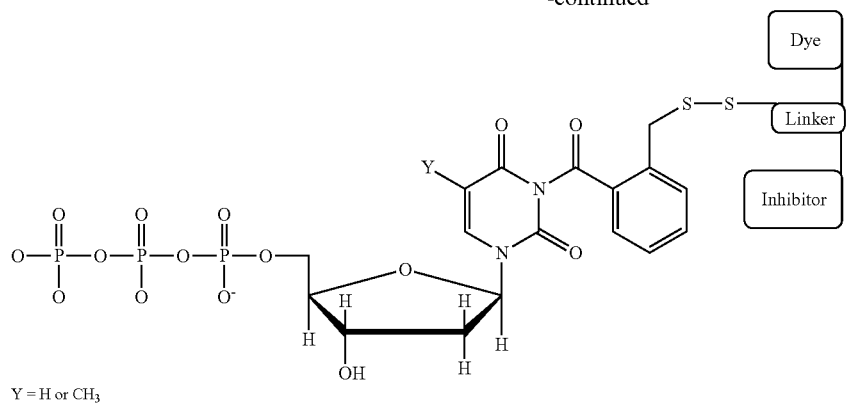

Y = H or CH₃

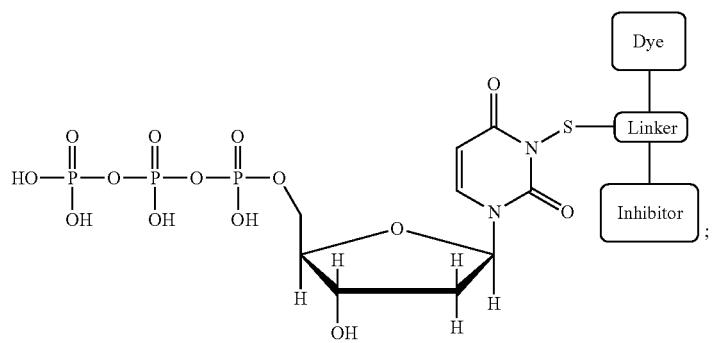

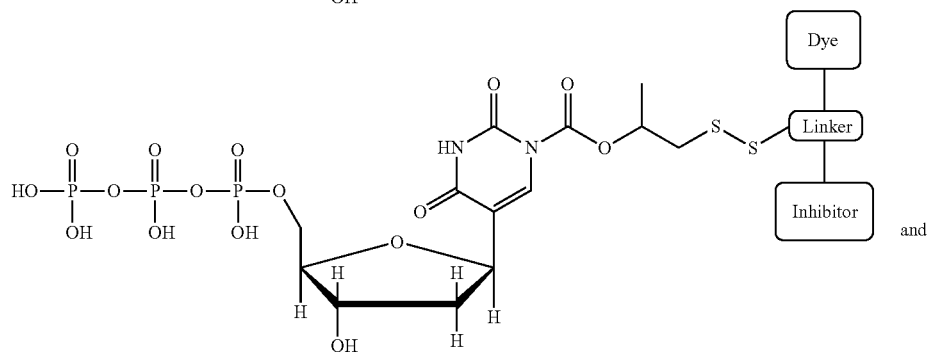

and

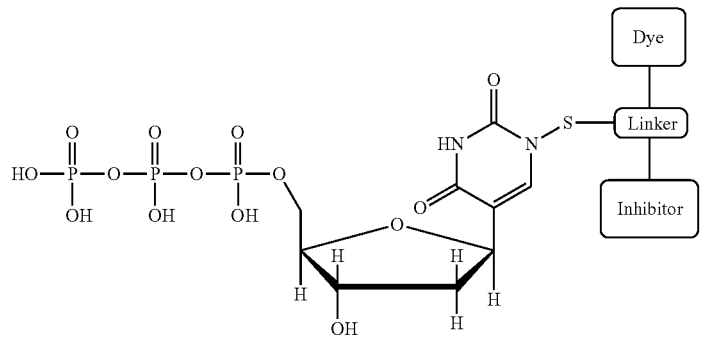

Upon contact of the nucleotide analogs of the invention with an activating agent, the detectable label is cleaved, and the linker is eliminated, thus producing a natural nucleotide. Exemplary activating agents that interact with the nucleotide analogs of the invention to cleave the label and eliminate the linker include reducing agents. Exemplary reducing agents include THP, TCEP, THPP, DTT, Cysteine, Glutathione, or combinations thereof. In certain embodiments, a single activating agent is used to cleave the detectable label and eliminate the linker. In other embodiments, multiple activating agents are used to cleave the detectable label and eliminate the linker. In certain embodiments, a combination of two different reducing agents is employed. In other embodiments, a combination of three different reducing agents is employed.

The following synthetic pathway shows a schematic of cleavage of the detectable label and elimination of the linker from the nucleotide analogs of the invention to produce a natural or near natural nucleotide after the nucleotide has been contacted with an activating agent.

Scheme 1
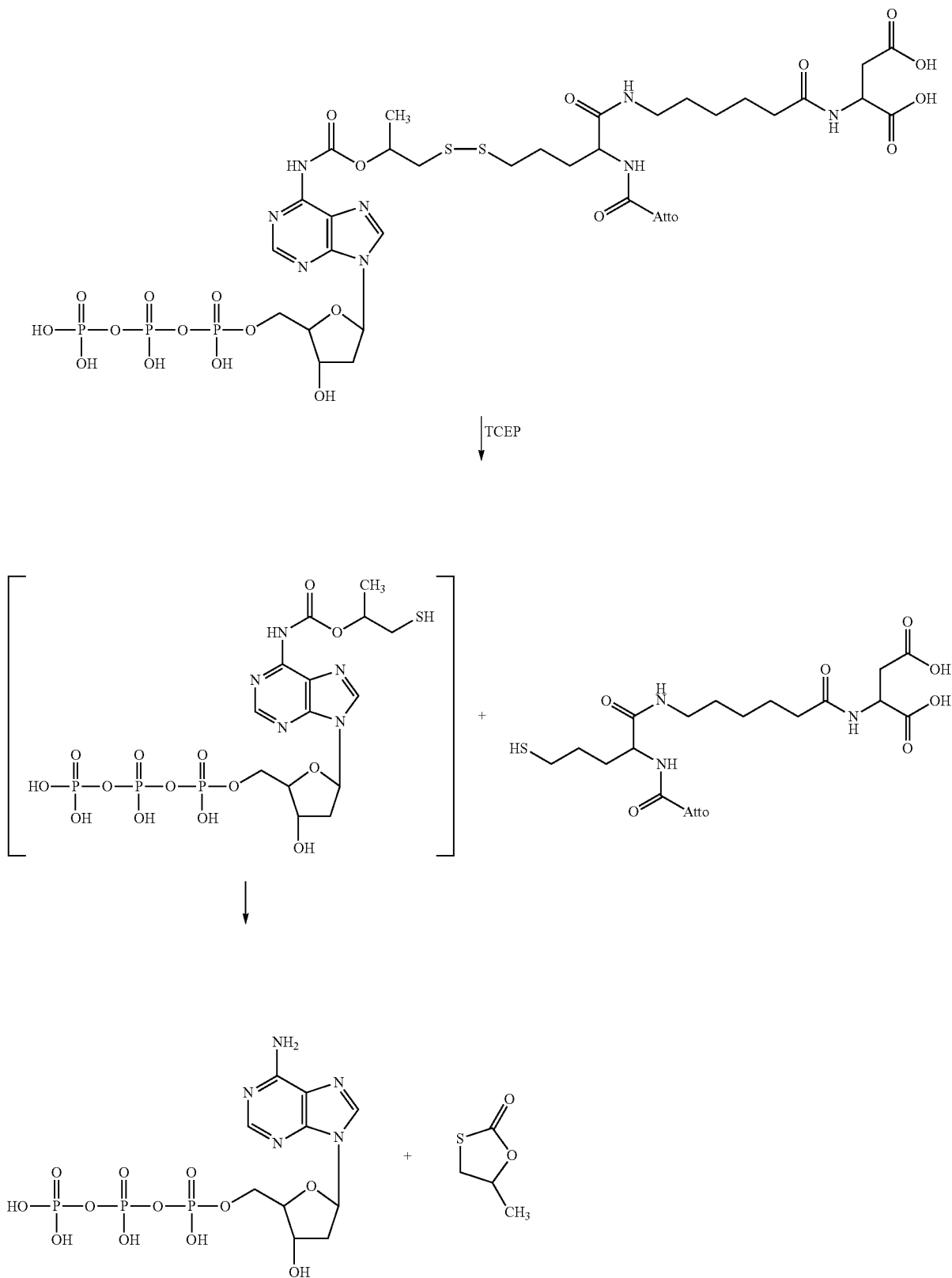

Scheme 2
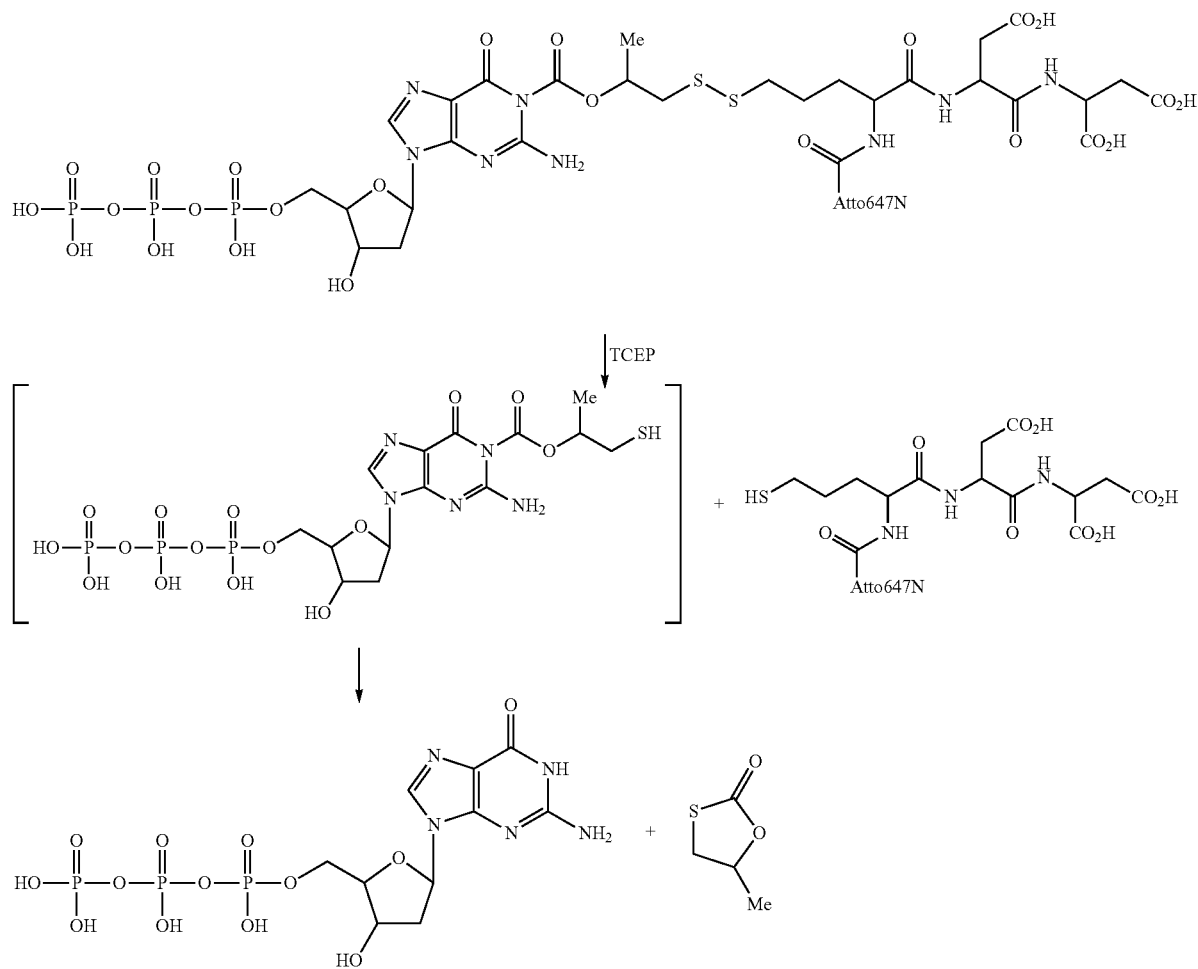
Scheme 3
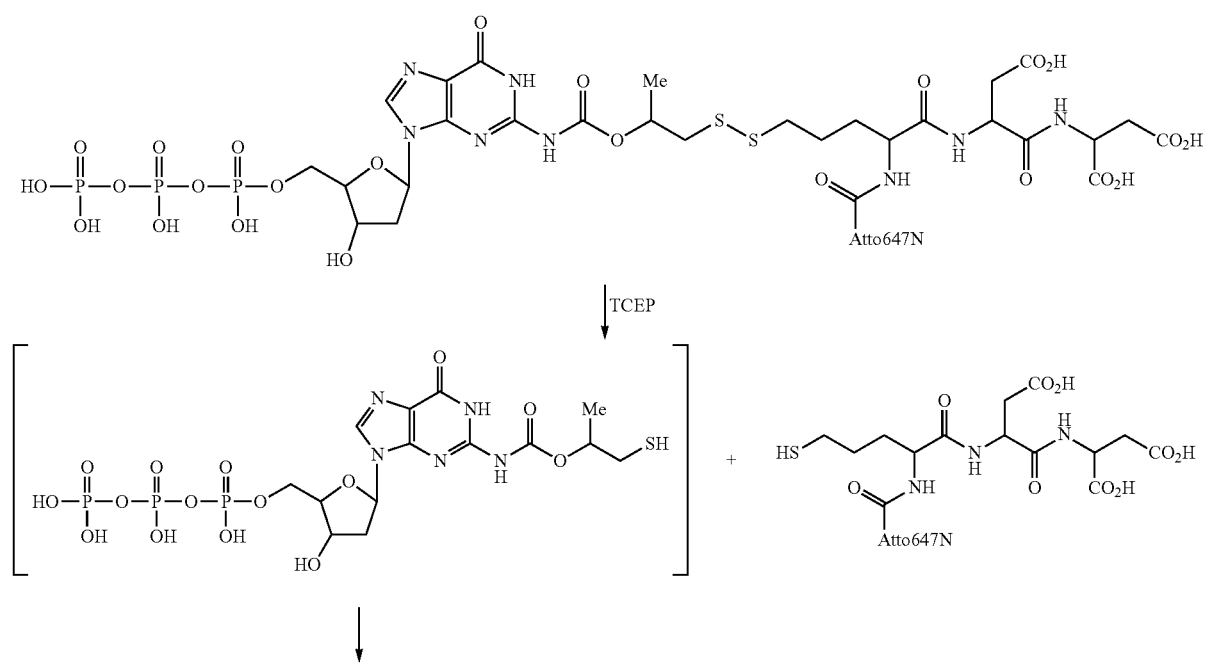

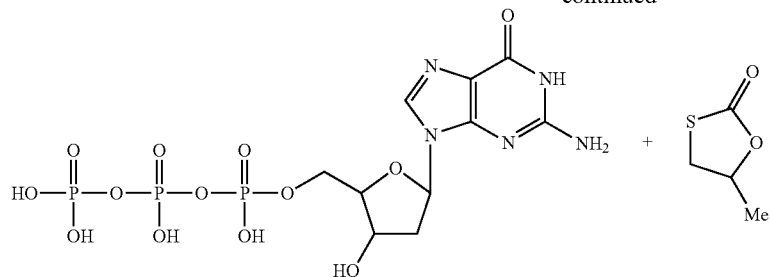
Scheme 4
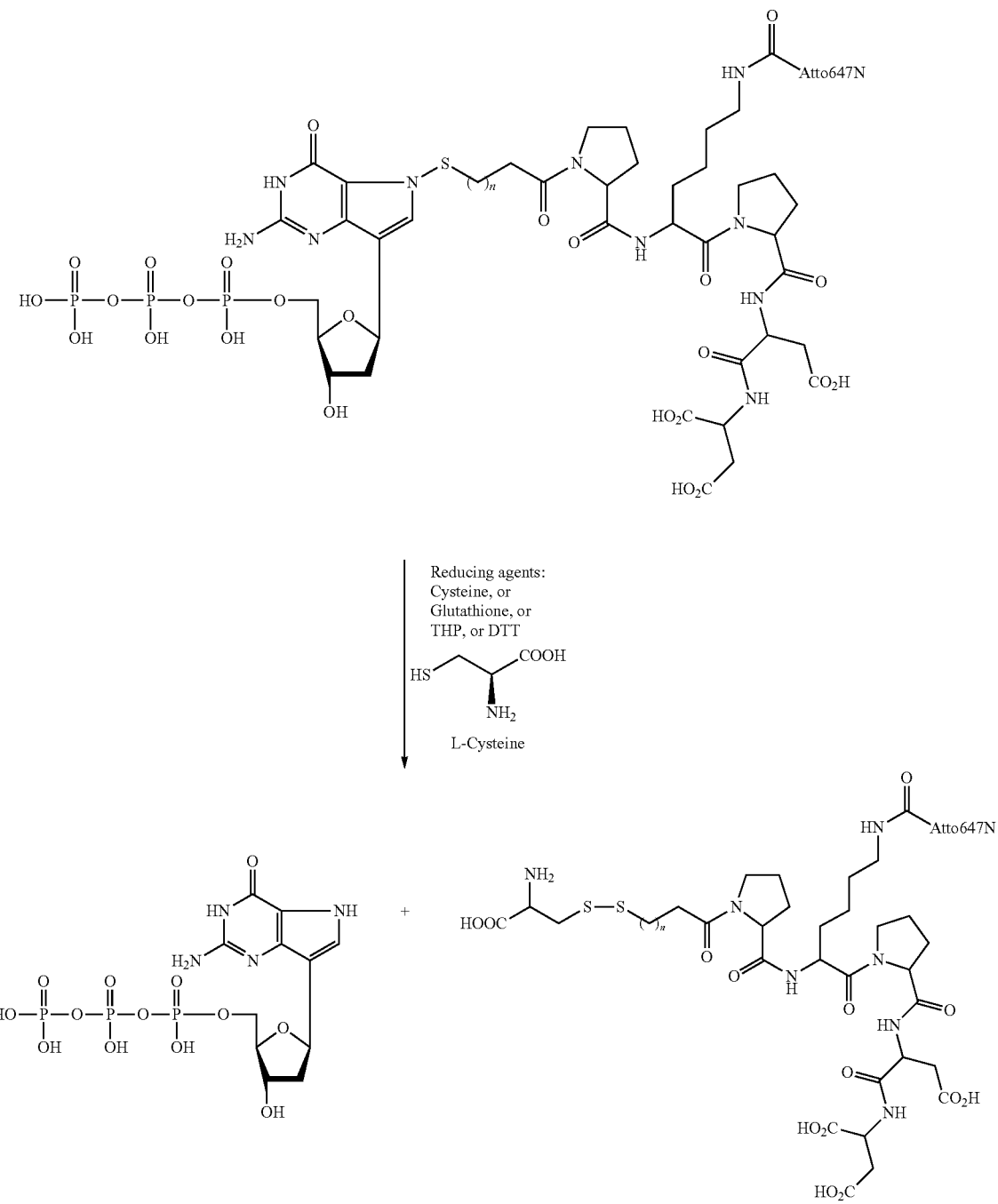

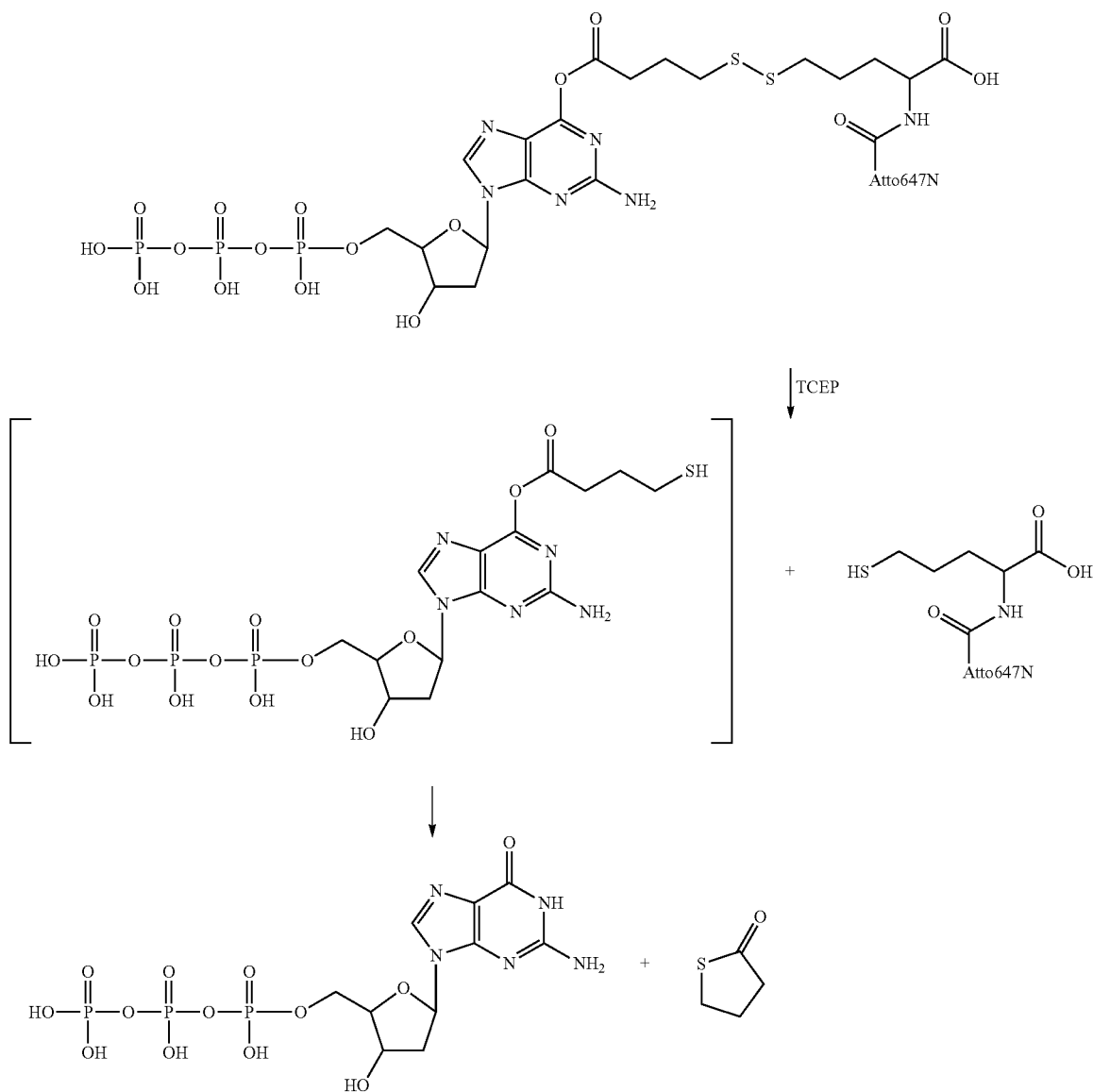
Scheme 5
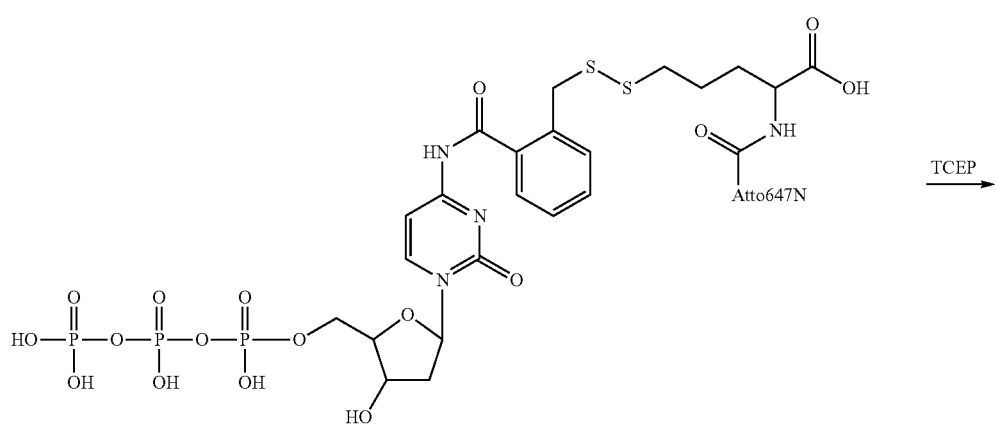
Scheme 6

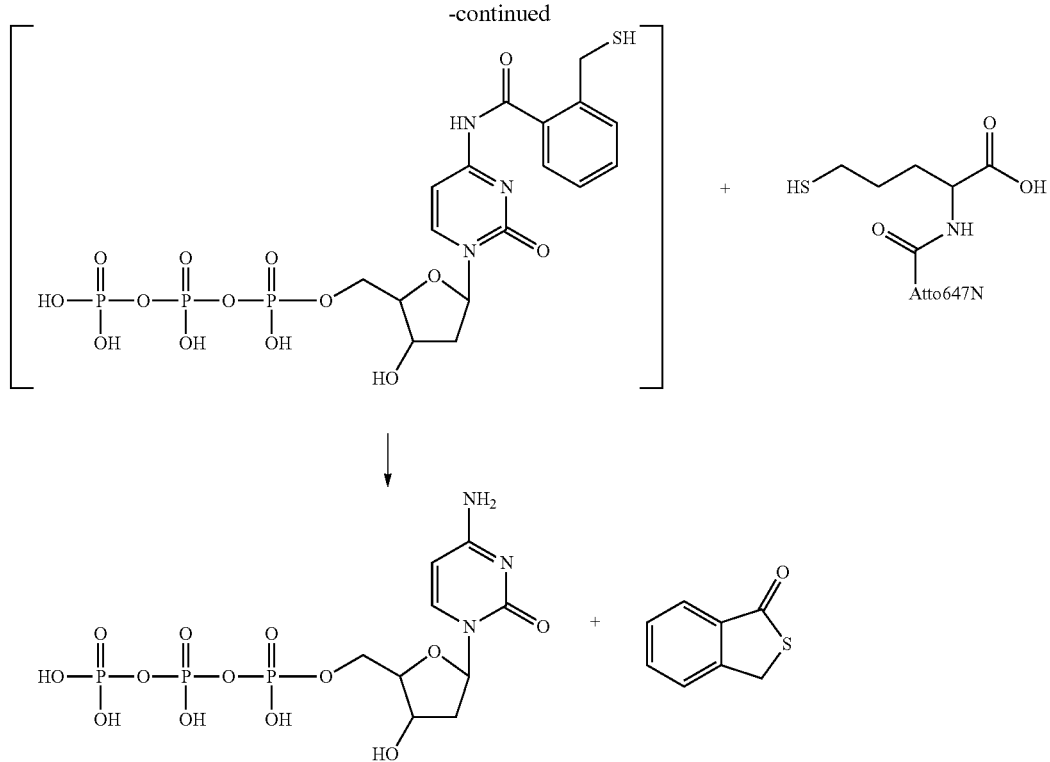
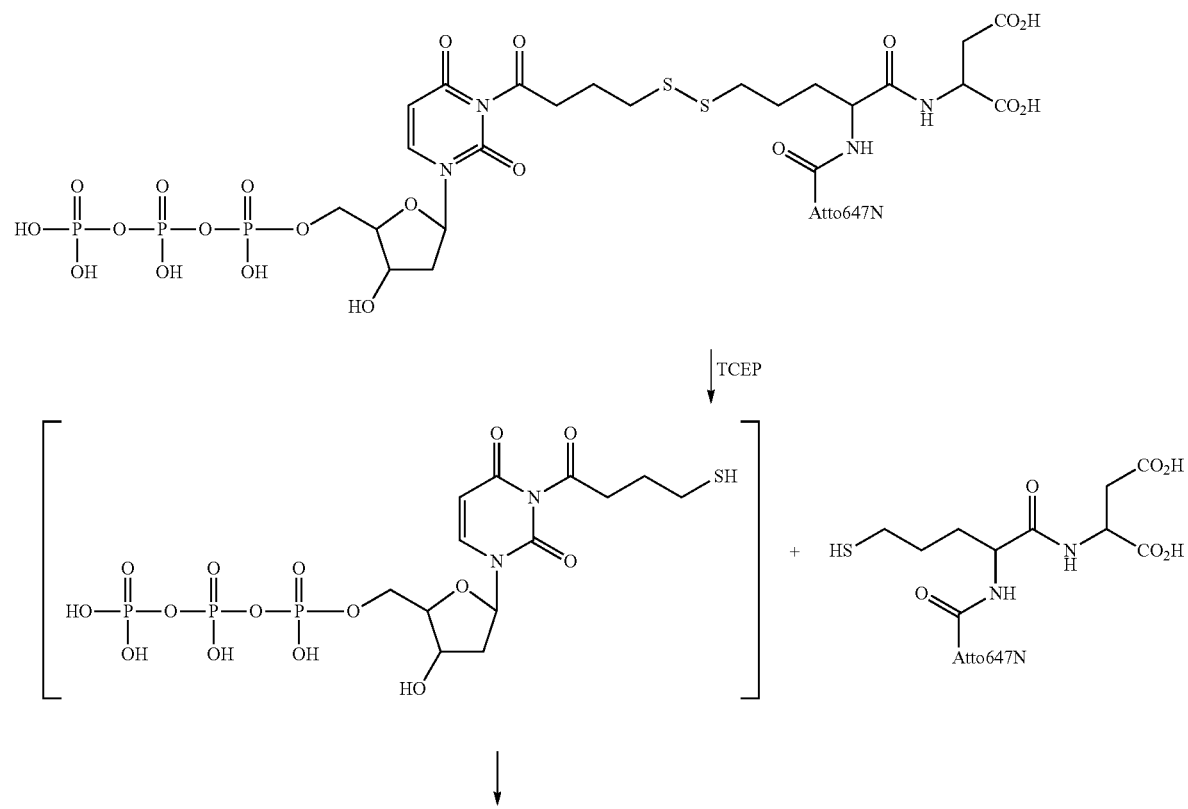
Scheme 7

-continued

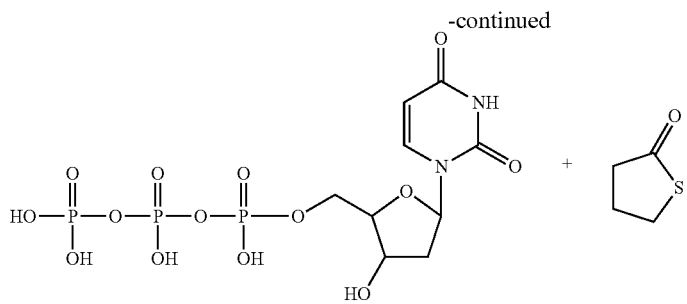

In another aspect, the invention provides nucleotide analogs that leave a minimal portion of the linker (i.e., capless nucleotide or post-incorporation modified nucleotide) connected to the nucleotide analog after cleavage of the label. Those nucleotide analogs of the invention include a linker having chemistry such that after cleavage of the label, a portion of the linker that remains connected to the nucleotide analog is neutral in charge.

In certain embodiments, these nucleotide analogs of the invention include a linker having chemistry such that after cleavage of the label and the first portion of the linker, the second portion of the linker does not require any subsequent chemical modification to render it neutral in charge, i.e., a capless nucleotide. In other embodiments, these nucleotide analogs of the invention include a linker having chemistry such that after cleavage of the label and the first portion of the linker, the second portion of the linker undergoes a subsequent chemical modification, rendering the second portion of the linker neutral in charge, i.e., post-incorporation modified nucleotide.

A linker having chemistry that produces a capless nucleotide or a linker having chemistry that produces a post-incorporation modified nucleotide ultimately produce the same type of nucleotide analog, i.e., a nucleotide analog in which a portion of the linker that remains attached to the nucleotide is neutral in charge. Thus, even though a portion of the linker remains after cleavage of the detectable label, the lack of charge on the remaining portion of the linker renders a nascent strand of DNA or RNA with properties that do not effect or are enhancing to addition of the next detectable incorporation. Therefore these analogs provide the same benefits as nucleotide analogs that revert to native nucleotides with respect to length of read or yield to length of the nascent strand of DNA or RNA.

The linker may be connected to any atom on a nucleotide. In certain embodiments, the linker is connected to any of the atoms of the nitrogenous base portion of the nucleotide analog. For example, the linker may be attached to N3 of the base when the base is thymine or uracil, attached to N4 of the base when the base is cytosine or adenine, attached to N2 of the base when the base is guanine, or attached to N7 of the base when the base is 9-deaza-G or 9-deaza-A or N5 of the base when the base is ψ-uridine. Alternatively, the linker may be attached to C5 of the base when the base is thymine, cytosine, or uracil, or attached to C7 of the base when the base is adenine or guanine if a near-native residual scar is generated after cleavage of the linker.

Upon contact of the nucleotide analogs of the invention with an activating agent, the detectable label and the first portion of the linker is cleaved, and the second portion that remains attached to the nucleotide is neutral in charge. Exemplary activating agents that interact with the nucleotide analogs of the invention to cleave the label and eliminate the linker include reducing agents. Exemplary reducing agents include TCEP, THP, DDT, THPP, cysteine, glutathione, or combinations thereof. In certain embodiments, a single activating agent is used to cleave the detectable label and eliminate the linker. In other embodiments, multiple activating agents are used to cleave the detectable label and eliminate the linker. In other embodiments, multiple activating agents are used to cleave the detectable label and eliminate the linker then modify the remaining linker using an alkylating agent or capping reagent. Exemplary alkylating agents or capping reagents include iodoacetamide, haloalkanes, α-haloketones, haloalkenes, haloalkynes. In certain embodiments, a combination of two different reducing and alkylating agents is employed. In other embodiments, a combination of three different reducing and alkylating agents is employed.

Exemplary structures of nucleotide analogs of the invention that produce a nucleotide having a neutrally charged portion of a linker remaining attached to the nucleotide after cleavage of the label (capless or post-incorporation modified) include:

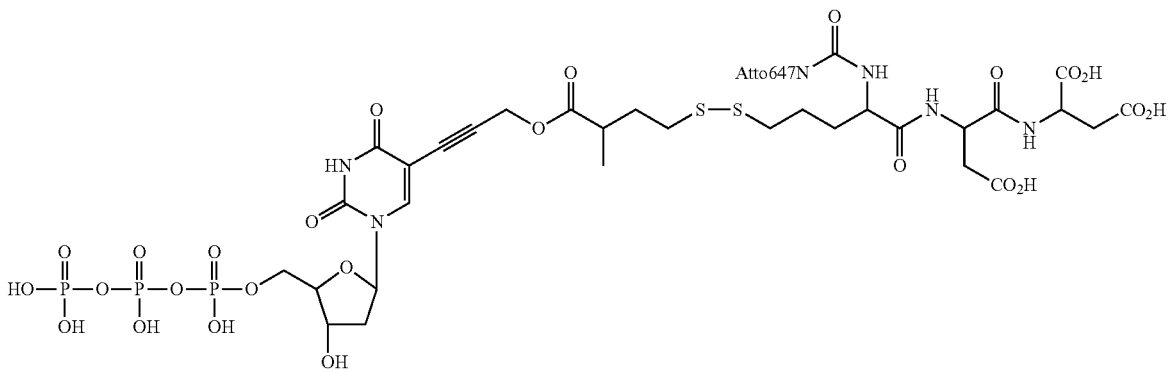

-continued
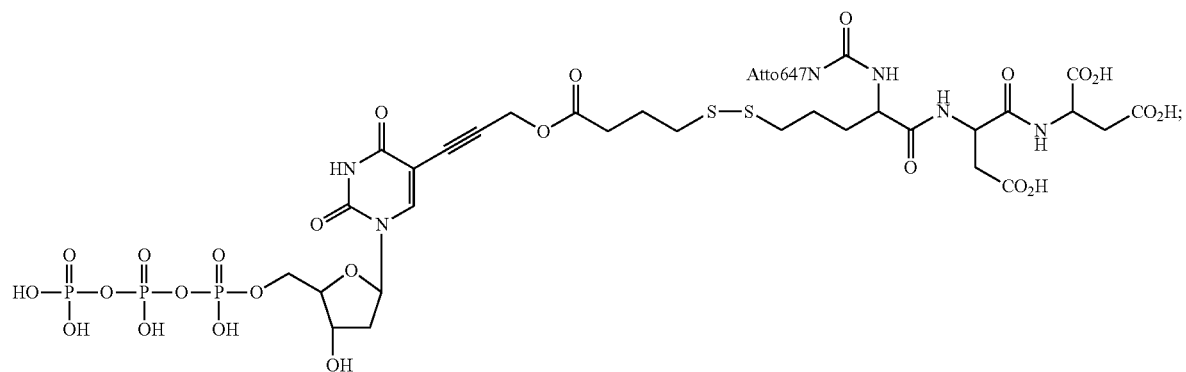
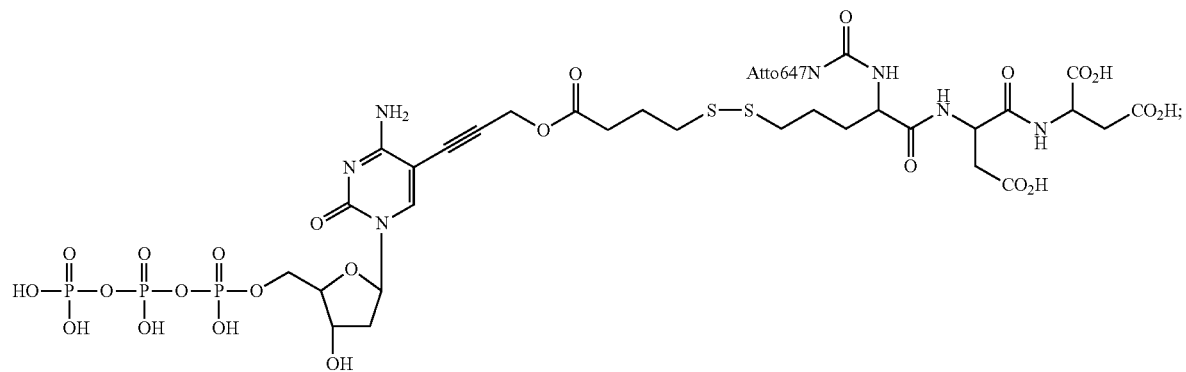
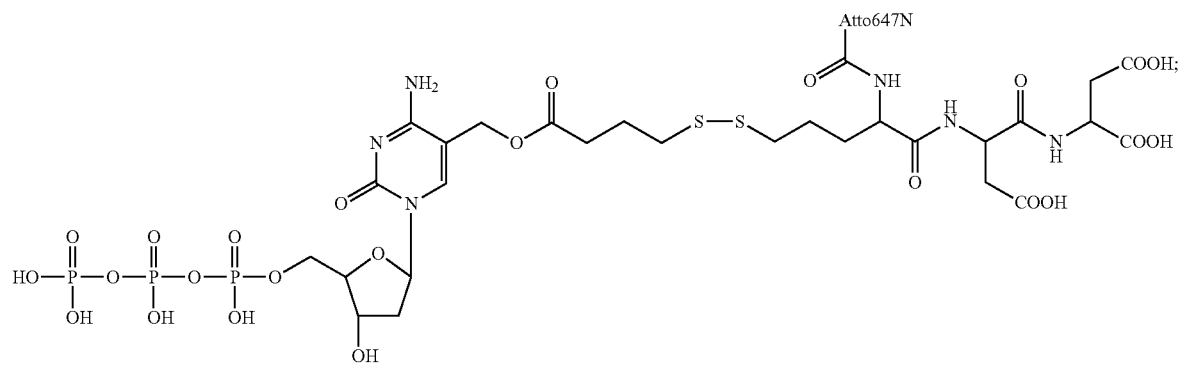
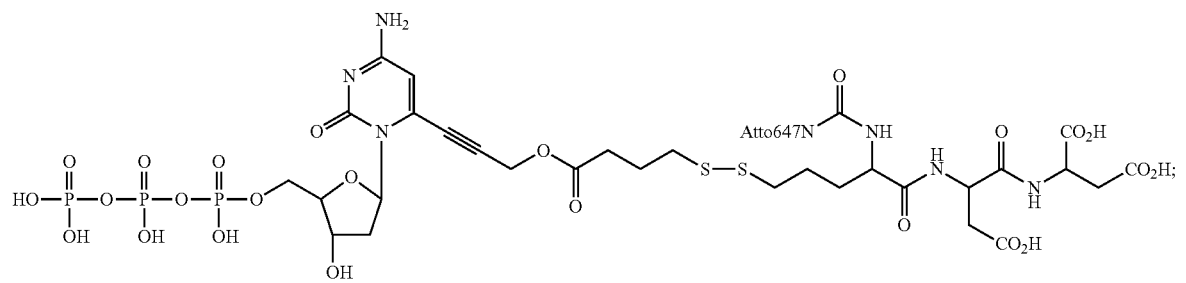

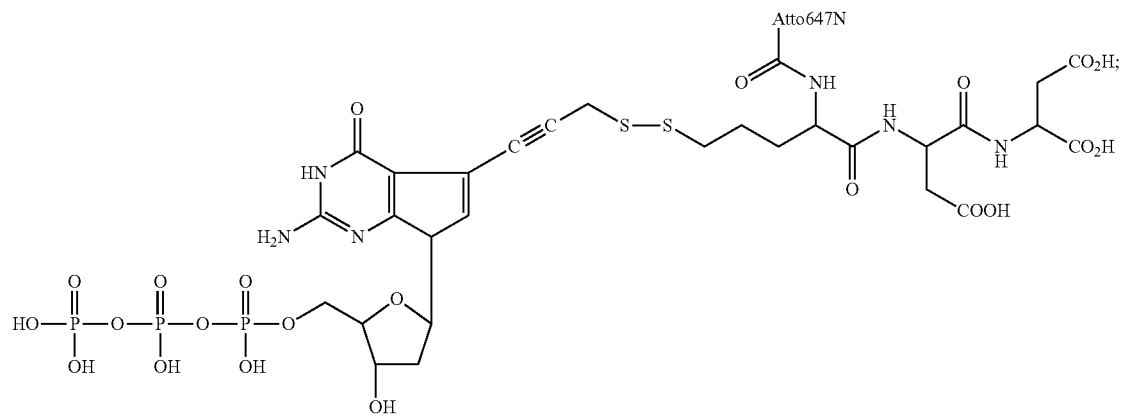
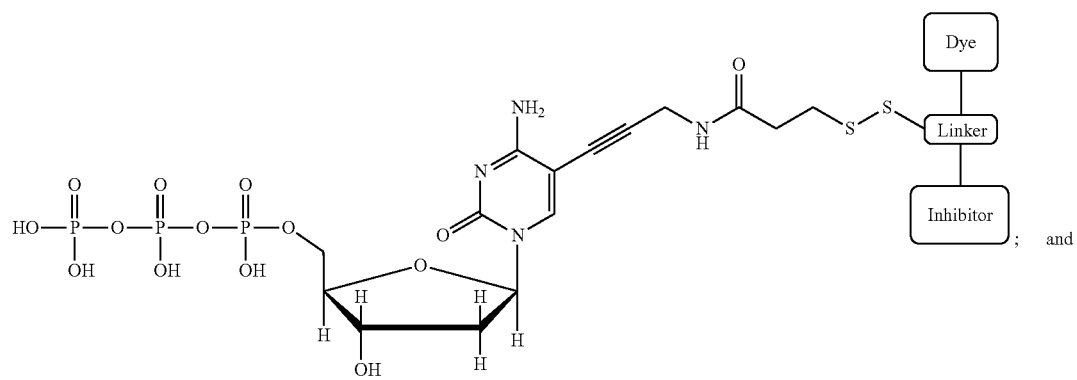
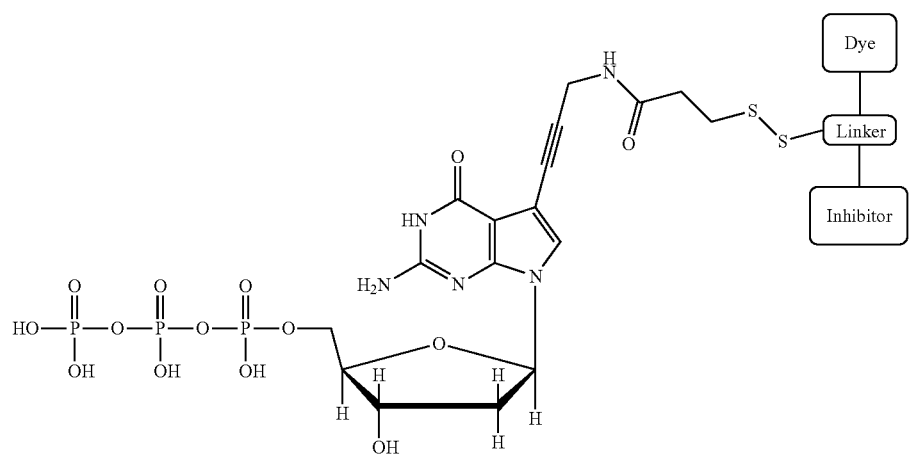
The following reaction pathways show a schematic for producing a capless nucleotide and a post-incorporation modified nucleotide from the analogs shown above after incorporation into an primer-template duplex.

Scheme 8
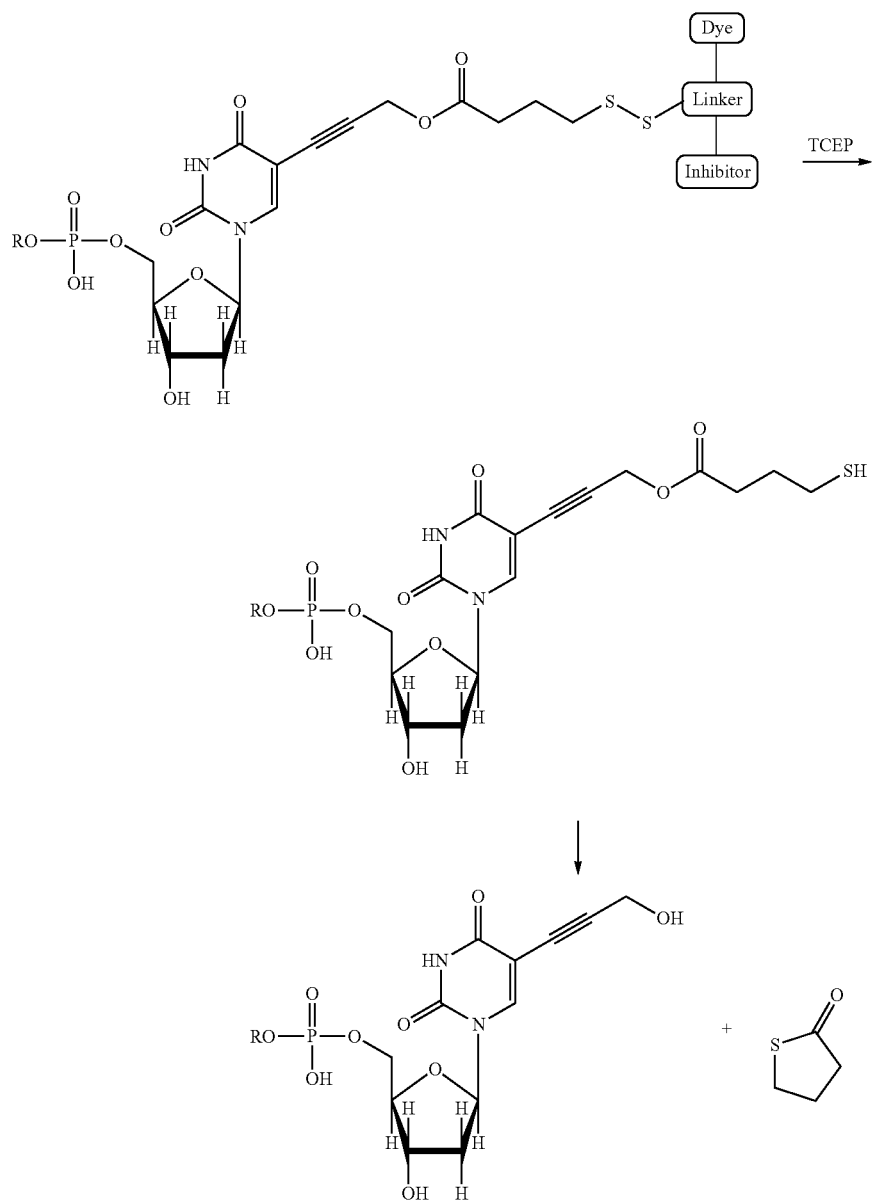
Scheme 9
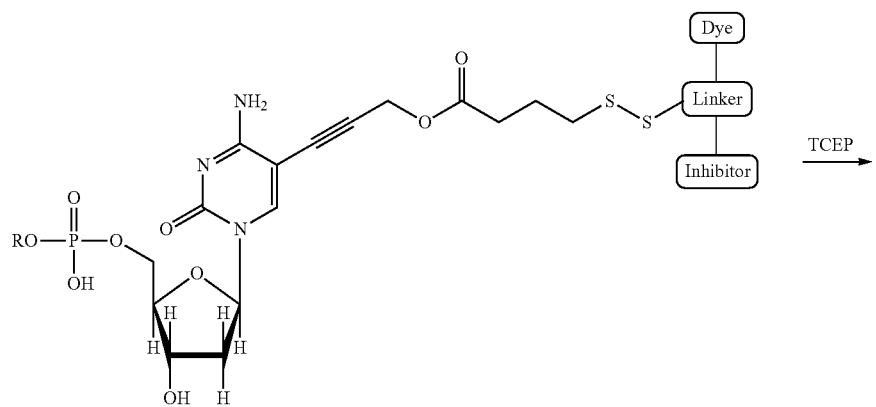

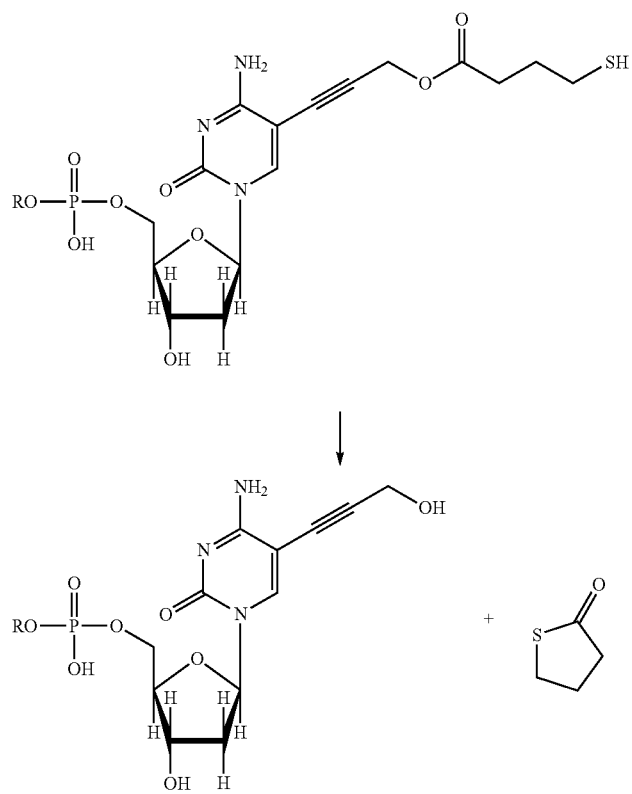
Scheme 10
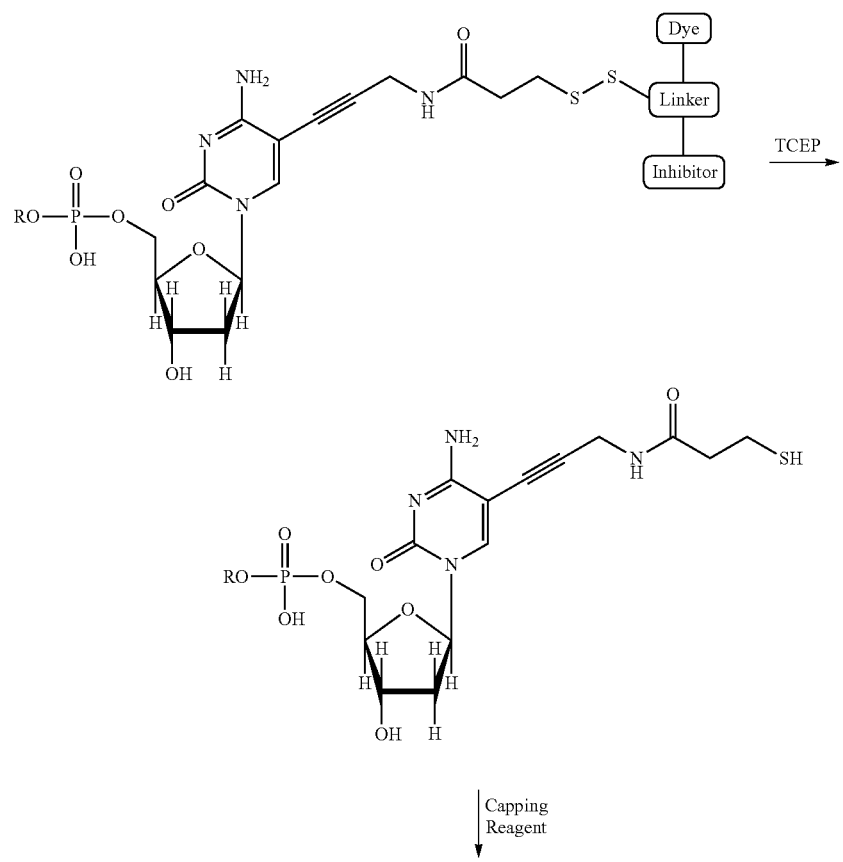

-continued
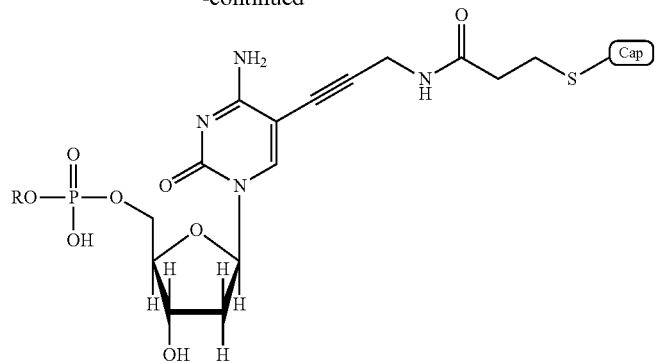
Scheme 11
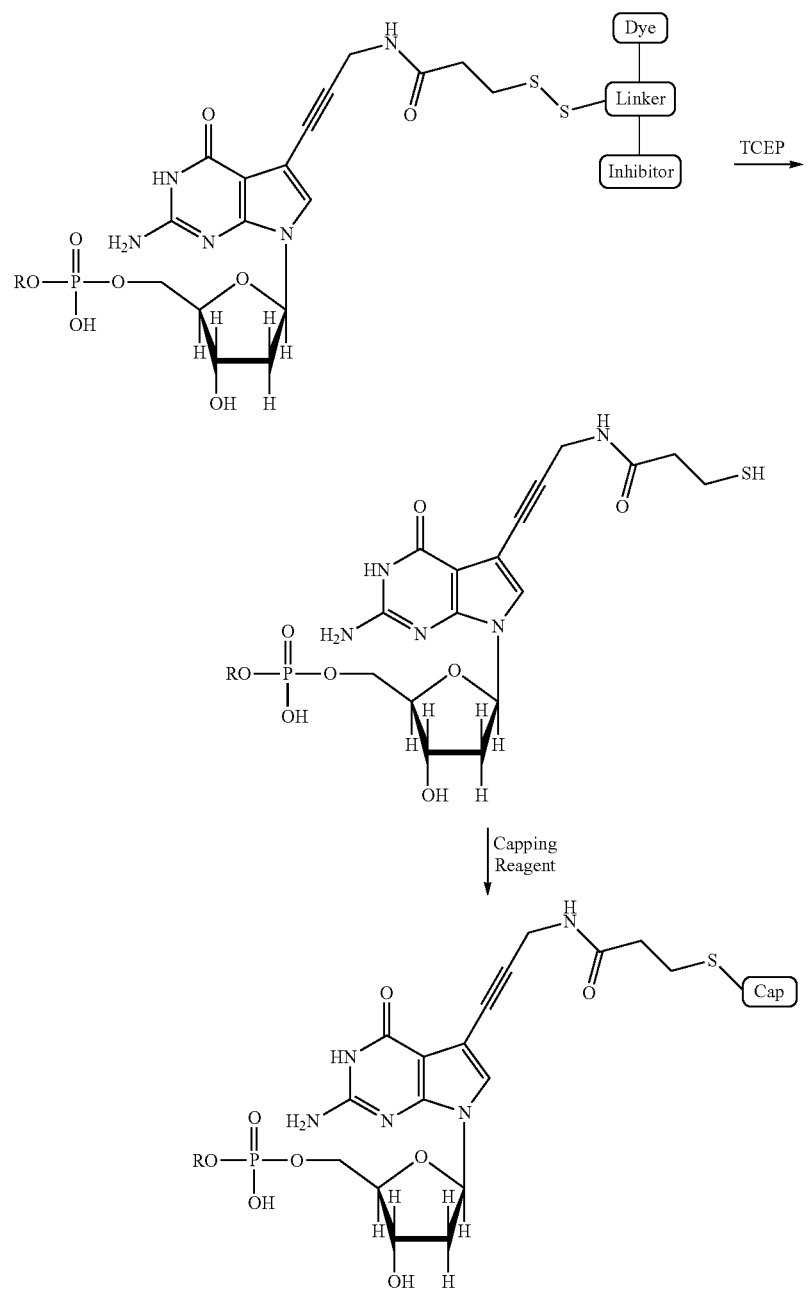

Scheme 12

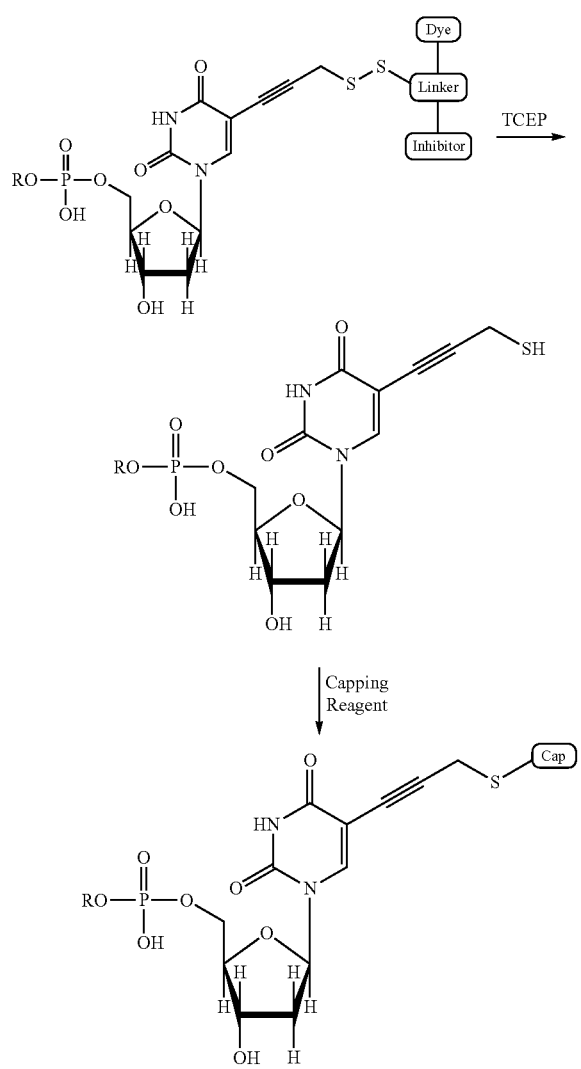

A non-exhaustive list of "Cap" includes:

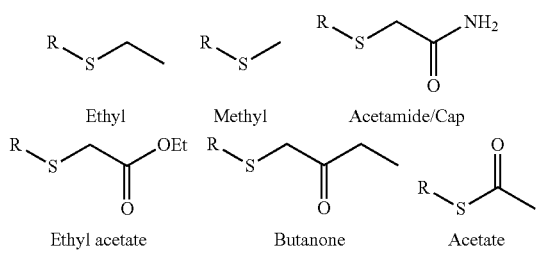

Nucleotide analogs of the invention generally include detectable labels. The detectable label may be directly or indirectly detectable. In certain embodiments, the exact label may be selected based, at least in part, on the particular type of detection method used. Exemplary detection methods include radioactive detection, optical absorbance detection, e.g., UV-visible absorbance detection, optical emission detection, e.g., fluorescence; phosphorescence or chemiluminescence; Raman scattering. Preferred labels include optically-detectable labels, such as fluorescent labels. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Atto dyes, Cy3; Cy5; Cy5.5; Cy7; IRD 700; IRD 800; La Jolta Blue; phthalo cyanine; and naphthalo cyanine. Preferred fluorescent labels are cyanine-3 and cyanine-5. Labels other than fluorescent labels are contemplated by the invention, including other optically-detectable labels.

Fluorescently labeled nucleotides may be produced by various techniques, such as those described in Kambara et al. (Bio/Technol., 6:816-21, 1988); Smith et al. (Nucl. Acid Res., 13:2399-2412, 1985); and Smith et al. (Nature, 321: 674-679, 1986). The fluorescent dye may be linked to the deoxyribose by a linker arm that is easily cleaved by chemical or enzymatic means. There are numerous linkers and methods for attaching labels to nucleotides, as shown in Oligonucleotides and Analogues: A Practical Approach (IRL Press, Oxford, 1991); Zuckerman et al. (Polynucleotides Res., 15: 5305-5321, 1987); Sharma et al. (Polynucleotides Res., 19:3019, 1991); Giusti et al. (PCR Methods and Applications, 2:223-227, 1993); Fung et al. (U.S. Pat. No. 4,757,141); Stabinsky (U.S. Pat. No. 4,739,044); Agrawal et al. (Tetrahedron Letters, 31:1543-1546, 1990); Sproat et al. (Polynucleotides Res., 15:4837, 1987); and Nelson et al. (Polynucleotides Res., 17:7187-7194, 1989). Extensive guidance exists in the literature for derivatizing fluorophore and quencher molecules for covalent attachment via common reactive groups that may be added to a nucleotide. Many linking moieties and methods for attaching fluorophore moieties to nucleotides also exist, as described in Oligonucleotides and Analogues, supra; Guisti et al., supra; Agrawal et al, supra; and Sproat et al., supra.

The nucleotide analogs of the invention are useful for single color or four color detection; single molecule detection or ensemble detection such as by polonies, colonies, or single molecule colonies; and/or single molecule sequencing in discrete temporal steps, asynchronous steps, or in real-time. Any single molecule sequencing process that is limited by accumulation of non-natural DNA or RNA in the nascent strand would benefit from nucleotide analogs of the present invention. The nucleotide analogs of the invention are useful for any detectable label including non-optical detection methods such as, for example, detection using nanopores (e.g., protein or solid state) through which molecules are individually passed so as to allow identification of the molecules by noting characteristics or changes in various properties or effects such as capacitance or blockage current flow (see, for example, Stoddart et al, Proc. Nat. Acad. Sci., 106:7702, 2009; Purnell and Schmidt, ACS Nano, 3:2533, 2009; Branton et al, Nature Biotechnology, 26:1146, 2008; Polonsky et al, U.S. Application 2008/0187915; Mitchell & Howorka, Angew. Chem. Int. Ed. 47:5565, 2008; Borsenberger et al, J. Am. Chem. Soc., 131, 7530, 2009); or other suitable non-optical detection methods. Detectable labels can either be the same on all four nucleotide analogs (A, G, C, T, U) or different on each of the four nucleotide analogs (A, G, C, T, U).

Another aspect of the invention provides methods of sequencing nucleic acid molecules using nucleotide analogs of the invention described above. Sequencing methods described herein may utilize a single type of nucleotide analog described above, e.g., scarless, capless, and post-incorporated modified, in order to produce a nascent strand of DNA or RNA that is not inhibitory, or even enhances, the rate or extent of addition of the next detectable dNTP. Alternatively, sequencing methods described herein may utilize combinations of the nucleotide analogs described above in order to produce a nascent strand of DNA or RNA that is not inhibitory, or even enhances, the rate or extent of addition of the next detectable dNTP.

In certain embodiments, the sequencing method is a single molecule sequencing by synthesis method. Single molecule sequencing is shown for example in Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety. Briefly, a single-stranded nucleic acid (e.g., DNA or cDNA) is hybridized to oligonucleotides attached to a surface of a flow cell. The oligonucleotides may be covalently attached to the surface or various attachments other than covalent linking as known to those of ordinary skill in the art may be employed. Moreover, the attachment may be indirect, e.g., via a polymerase directly or indirectly attached to the surface. The surface may be planar or otherwise, and/or may be porous or non-porous, or any other type of surface known to those of ordinary skill to be suitable for attachment. The nucleic acid is then sequenced by imaging the polymerase-mediated addition of fluorescently-labeled nucleotides incorporated into the growing strand surface oligonucleotide, at single molecule resolution. The following sections discuss general considerations for nucleic acid sequencing, for example, template considerations, polymerases useful in sequencing-by-synthesis, choice of surfaces, reaction conditions, signal detection and analysis.

Nucleic Acid Templates

Nucleic acid templates include deoxyribonucleic acid (DNA) and/or ribonucleic acid (RNA). Nucleic acid templates can be synthetic or derived from naturally occurring sources. In one embodiment, nucleic acid template molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. Biological samples for use in the present invention include viral particles or preparations. Nucleic acid template molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid template molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA.

Nucleic acid obtained from biological samples typically is fragmented to produce suitable fragments for analysis. In one embodiment, nucleic acid from a biological sample is fragmented by sonication. Nucleic acid template molecules can be obtained as described in U.S. Patent Application Publication Number US2002/0190663 A1, published Oct. 9, 2003. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Generally, individual nucleic acid template molecules can be from about 5 bases to about 20 kb. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In a preferred embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-$C_6H_4$—($OCH_2$—$CH_2$)$_x$OH, x=9-10, Triton® X-100R, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulf-onate. It is contemplated also that urea may be added with or without another detergent or surfactant.

Lysis or homogenization solutions may further contain other agents, such as reducing agents. Examples of such reducing agents include dithiothreitol (DTT), .beta.-mercaptoethanol, DTE, GSH, cysteine, cysteamine, tricarboxyethyl phosphine (TCEP), or salts of sulfurous acid.

Nucleic Acid Polymerases

Nucleic acid polymerases generally useful in the invention include DNA polymerases, RNA polymerases, reverse transcriptases, and mutant or altered forms of any of the foregoing. DNA polymerases and their properties are described in detail in, among other places, DNA Replication 2nd edition, Kornberg and Baker, W. H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al., 1991, Polynucleotides Res, 19: 4193, New England Biolabs), 9.degree.Nm™ DNA polymerase (New England Biolabs), Stoffel fragment, ThermoSequenase® (Amersham Pharmacia Biotech UK), Therminator™ (New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J. Biol. Chem. 256:3112), and archaeal DP1I/DP2 DNA polymerase II (Cann et al, 1998, Proc. Natl. Acad. Sci. USA 95:14250).

Both mesophilic polymerases and *thermophilic* polymerases are contemplated. *Thermophilic* DNA polymerases include, but are not limited to, ThermoSequenase®, 9.degree.Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. A highly-preferred form of any polymerase is a 3' exonuclease-deficient mutant.

Reverse transcriptases useful in the invention include, but are not limited to, reverse transcriptases from HIV, HTLV-1, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al., CRC Crit. Rev Biochem. 3:289-347 (1975)).

Surfaces

In a preferred embodiment, nucleic acid template molecules are attached to a substrate (also referred to herein as a surface) and subjected to analysis by single molecule sequencing as described herein. Nucleic acid template molecules are attached to the surface such that the template/primer duplexes are individually optically resolvable. Substrates for use in the invention can be two- or three-dimensional and can comprise a planar surface (e.g., a glass slide) or can be shaped. A substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a nucleic acid. Substrates can include planar arrays or matrices capable of having regions that include populations of template nucleic acids or primers. Examples include nucleoside-derivatized CPG and polystyrene slides; derivatized magnetic slides; polystyrene grafted with polyethylene glycol, and the like.

Substrates are preferably coated to allow optimum optical processing and nucleic acid attachment. Substrates for use in the invention can also be treated to reduce background. Exemplary coatings include epoxides, and derivatized epoxides (e.g., with a binding molecule, such as an oligonucleotide or streptavidin).

Various methods can be used to anchor or immobilize the nucleic acid molecule to the surface of the substrate. The immobilization can be achieved through direct or indirect bonding to the surface. The bonding can be by covalent linkage. See, Joos et al., Analytical Biochemistry 247:96-101, 1997; Oroskar et al., Clin. Chem. 42:1547-1555, 1996; and Khandjian, Mol. Bio. Rep. 11:107-115, 1986. A preferred attachment is direct amine bonding of a terminal nucleotide of the template or the 5' end of the primer to an epoxide integrated on the surface. The bonding also can be through non-covalent linkage. For example, biotin-streptavidin (Taylor et al., J. Phys. D. Appl. Phys. 24:1443, 1991) and digoxigenin with anti-digoxigenin (Smith et al., Science 253:1122, 1992) are common tools for anchoring nucleic acids to surfaces and parallels. Alternatively, the attachment can be achieved by anchoring a hydrophobic chain into a lipid monolayer or bilayer. Other methods for known in the art for attaching nucleic acid molecules to substrates also can be used.

Detection

Any detection method can be used that is suitable for the type of label employed. Thus, exemplary detection methods include radioactive detection, optical absorbance detection, e.g., UV-visible absorbance detection, optical emission detection, e.g., fluorescence or chemiluminescence. For example, extended primers can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus, such as described in Fodor (U.S. Pat. No. 5,445,934) and Mathies et al. (U.S. Pat. No. 5,091, 652). Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993), such as described in Yershov et al., Proc. Natl. Acad. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. Such detection methods are particularly useful to achieve simultaneous scanning of multiple attached template nucleic acids.

A number of approaches can be used to detect incorporation of fluorescently-labeled nucleotides into a single nucleic acid molecule. Optical setups include near-field scanning microscopy, far-field confocal microscopy, wide-field epi-illumination, light scattering, dark field microscopy, photoconversion, single and/or multiphoton excitation, spectral wavelength discrimination, fluorophor identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Some embodiments of the present invention use TIRF microscopy for imaging. TIRF microscopy uses totally internally reflected excitation light and is well known in the art. See, e.g., the World Wide Web at nikon-instruments.jp/eng/page/products/tirf.aspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. The optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the attached template/primer complex in the presence of a polymerase. Total internal reflectance fluorescence microscopy is then used to visualize the attached template/primer duplex and/or the incorporated nucleotides with single molecule resolution.

Analysis

Alignment and/or compilation of sequence results obtained from the image stacks produced as generally described above utilizes look-up tables that take into account possible sequences changes (due, e.g., to errors, mutations, etc.). Essentially, sequencing results obtained as described herein are compared to a look-up type table that contains all possible reference sequences plus 1 or 2 base errors.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

EXAMPLES

Example 1

Nucleotide Analogs of the Invention Improve Sequencing Efficiency

A problem encountered during single molecule sequencing reactions that use nucleotide analogs that have a detectable label and/or inhibitory group attached to the nucleotide through a cleavage linker is that upon cleavage of the linker on the incorporated nucleotide a scar-bearing nucleotide is generated. After several cycles of incorporation and cleavage, a nascent strand of DNA or RNA including multiple scar-bearing nucleotides is produced, resulting in a highly modified polynucleotide with properties that inhibit rate of efficiency of incorporation of the next labeled nucleotide. A decrease in the rate of efficiency of incorporation of the next labeled nucleotide has the cumulative effect of limiting the rate of growth of the nascent strand of DNA or RNA or limiting the length of the nascent strand of DNA or RNA. A net result is limitation of an observed length of read (LOR) or a limitation of a yield to length (YTL) of the nascent strand of DNA or RNA.

FIG. 1 shows an example in which a scarless A analog is included in a mixture with three non-scarless analogs. Data in this figure show dramatic improvements in efficiency of incorporation through certain sequence contexts ($A_3, A_4, A_5$).

Example 2

Figure 2:
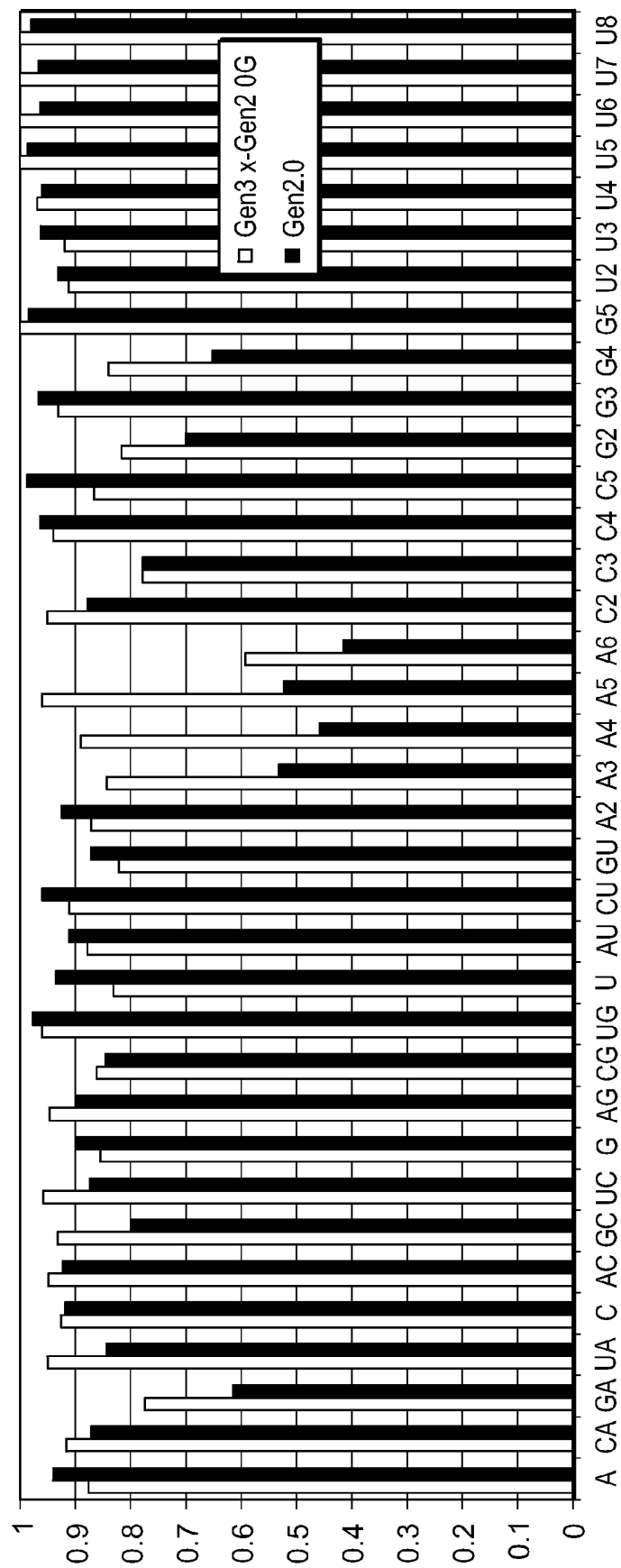
FIG. 2 is a graph showing a comparison of the efficiency of next base addition for a number of specific sequence contexts using detectable dNTP analogs of dA and dU.
Figure 3:
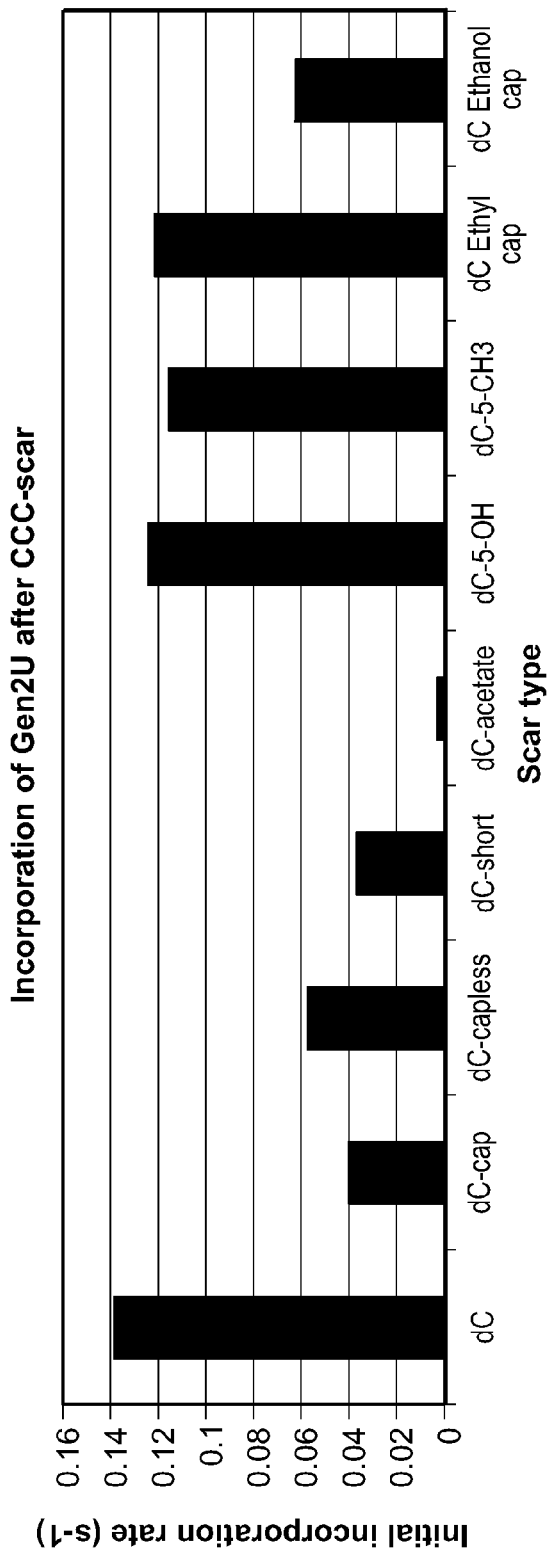
FIG. 3 is a graph showing next base incorporation rate over multiple incorporated dC scars, comparing rate impact of different chemical modifications of incorporated scars.
Figure 4:
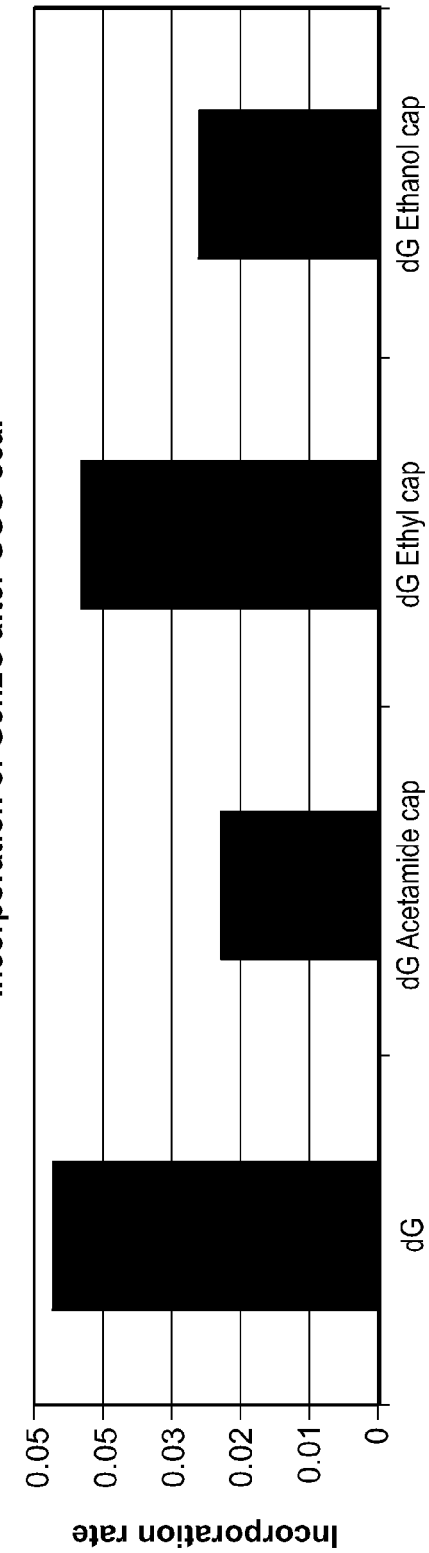
FIG. 4 is a graph showing next base incorporation rate over multiple incorporated dG scars, comparing rate impact of different chemical modifications of incorporated scars.

Differing Effects of Nucleotide Analogs of the Invention on Next Base Incorporation FIGS. 2 and 3 provide data showing differing next base incorporation kinetics that were encountered with different types of nucleotide analogs of the invention. FIG. 2 is a graph showing next base incorporation rate over multiple incorporated dC scars, comparing rate impact of different chemical modifications of incorporated scars. FIG. 3 is a graph showing next base incorporation rate over multiple incorporated dG scars, comparing rate impact of different chemical modifications of incorporated scars. The different analogs were generated using different alkylating agents to produce different post-incorporation modified nucleotides after incorporation of the detectably labeled nucleotide and cleavage of the label and first portion of the linker.

Example 3
Synthetic Scheme 9 Deaza dGTP
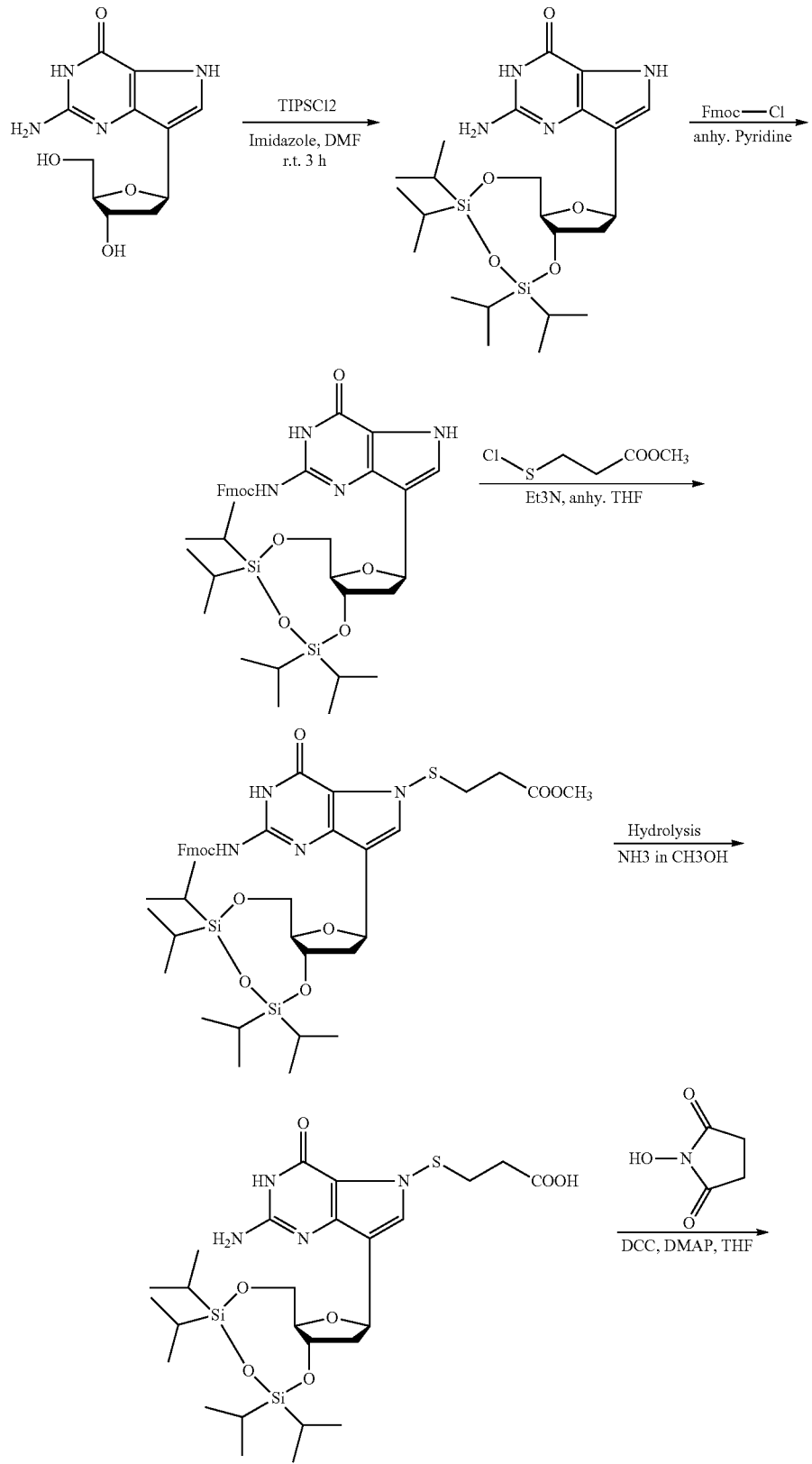

-continued
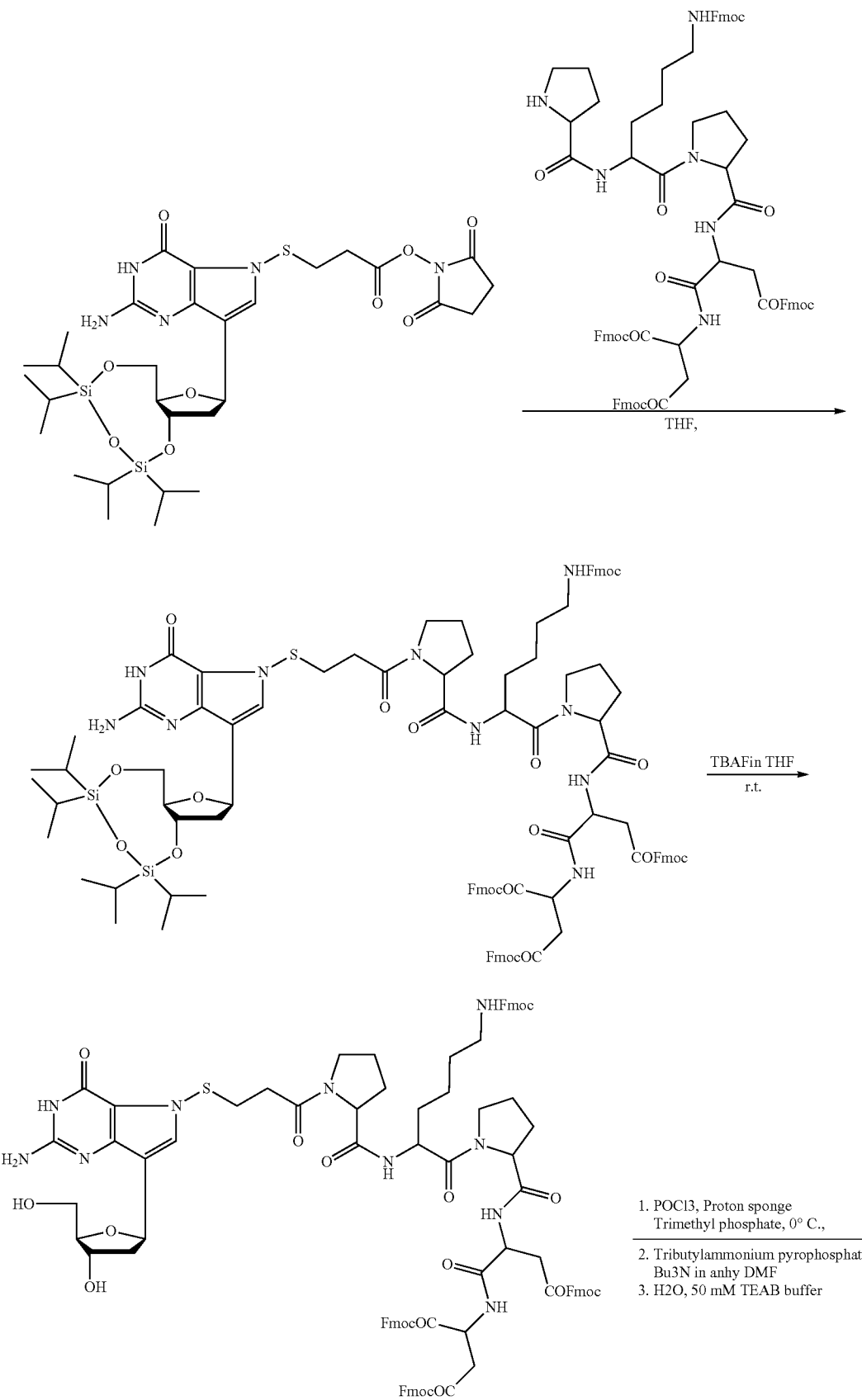

-continued
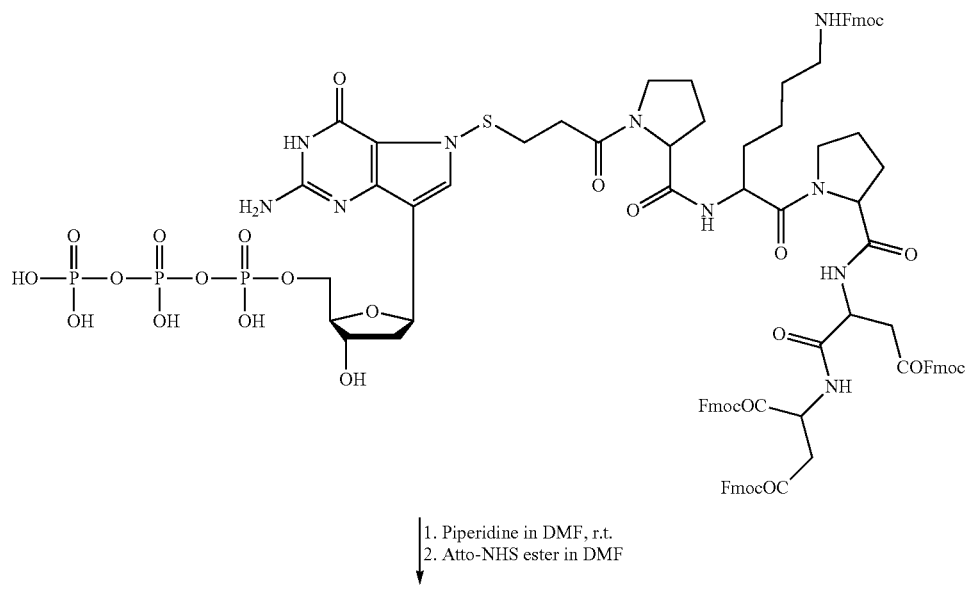
1. Piperidine in DMF, r.t.
2. Atto-NHS ester in DMF
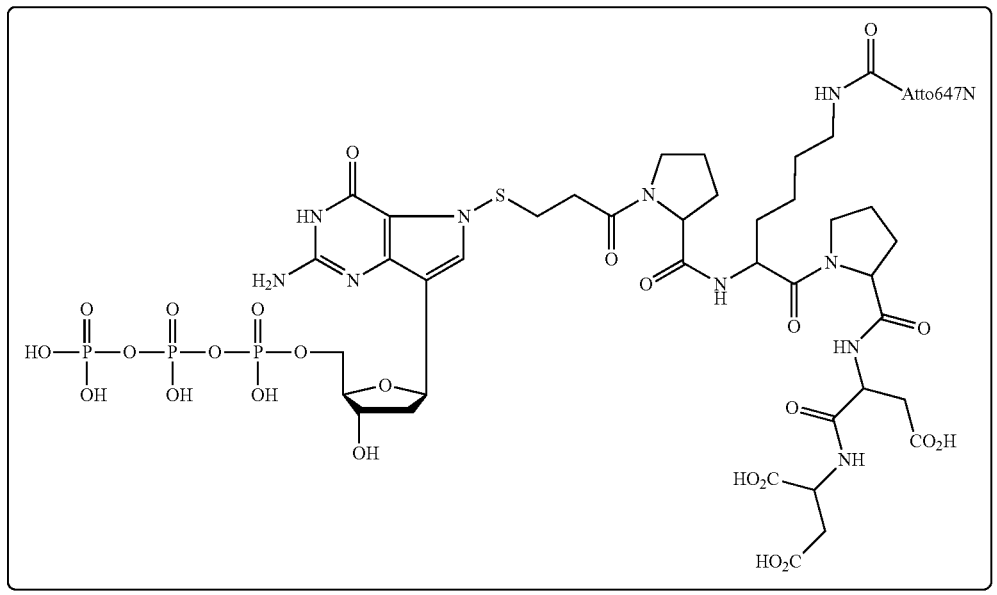

Example 4
Scarless dUTP Synthesis
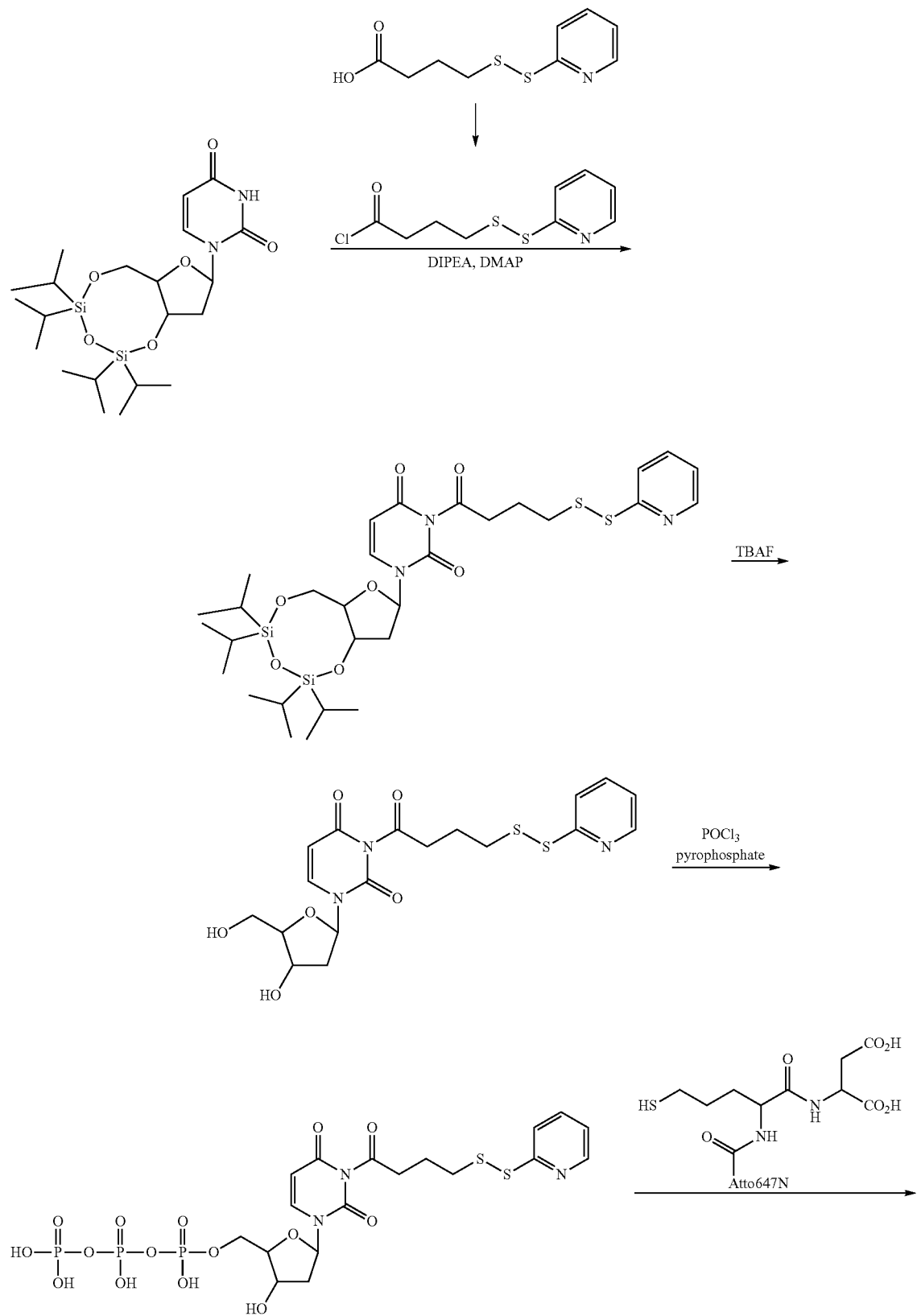

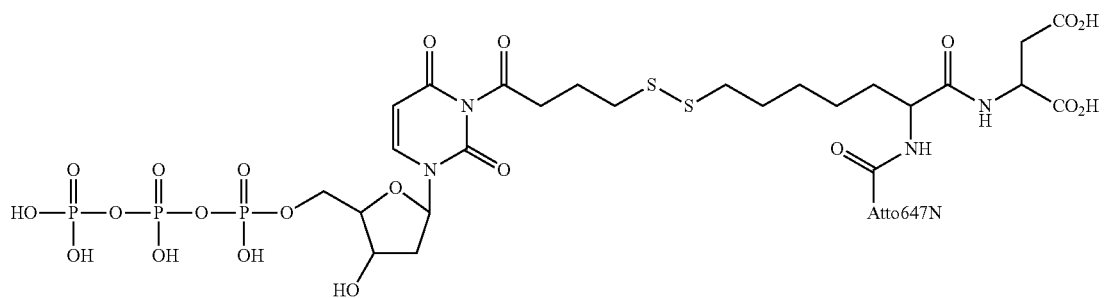
Example 5
Scarless dATP Synthesis Example
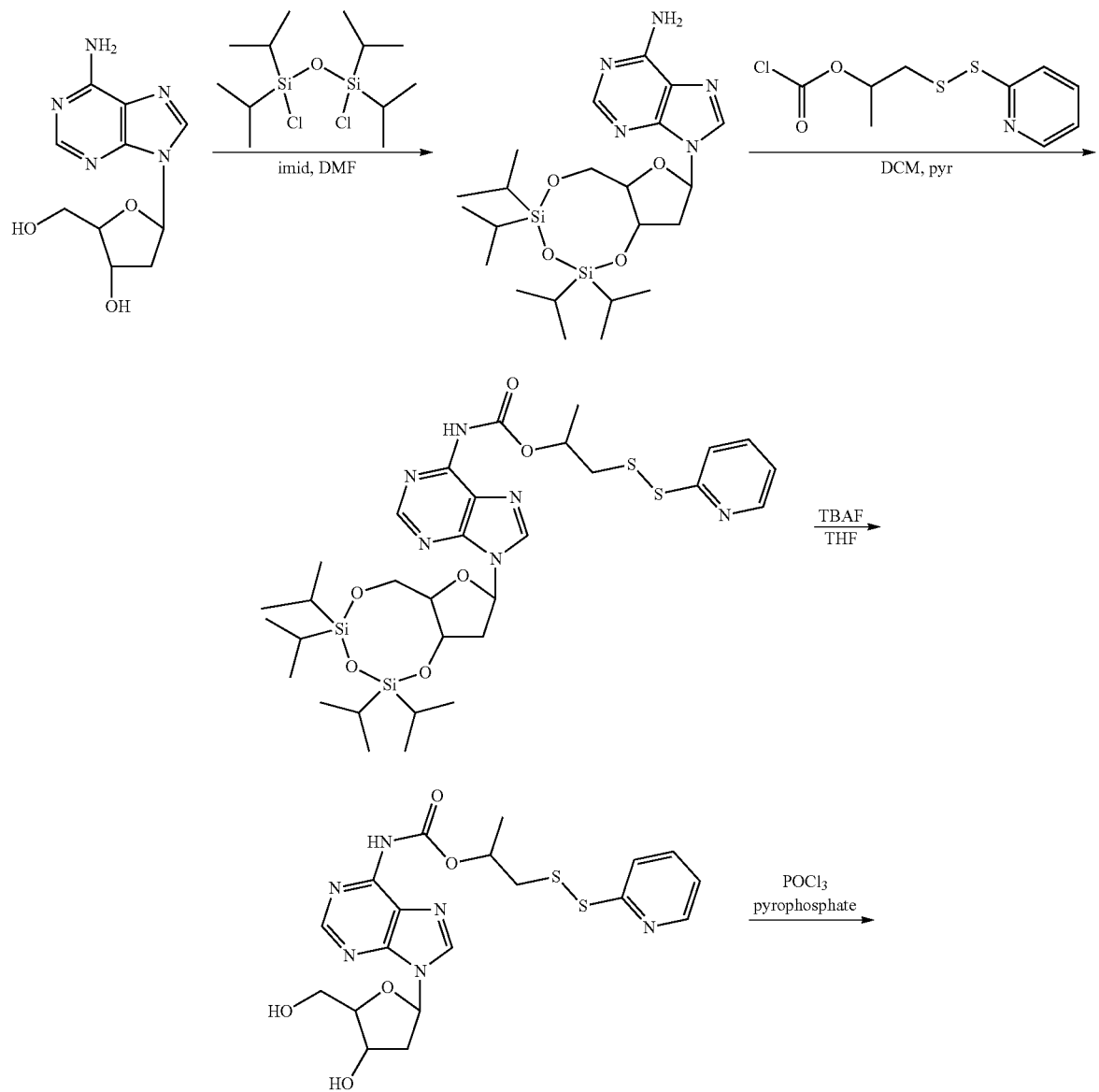

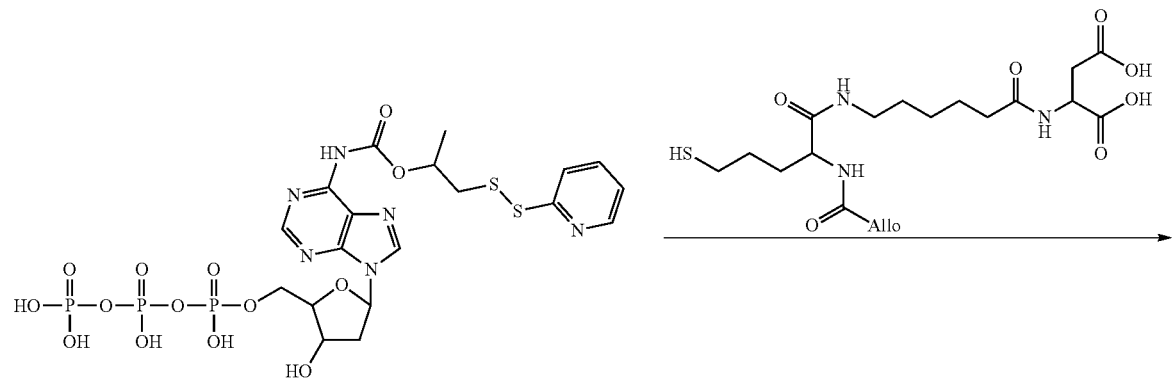
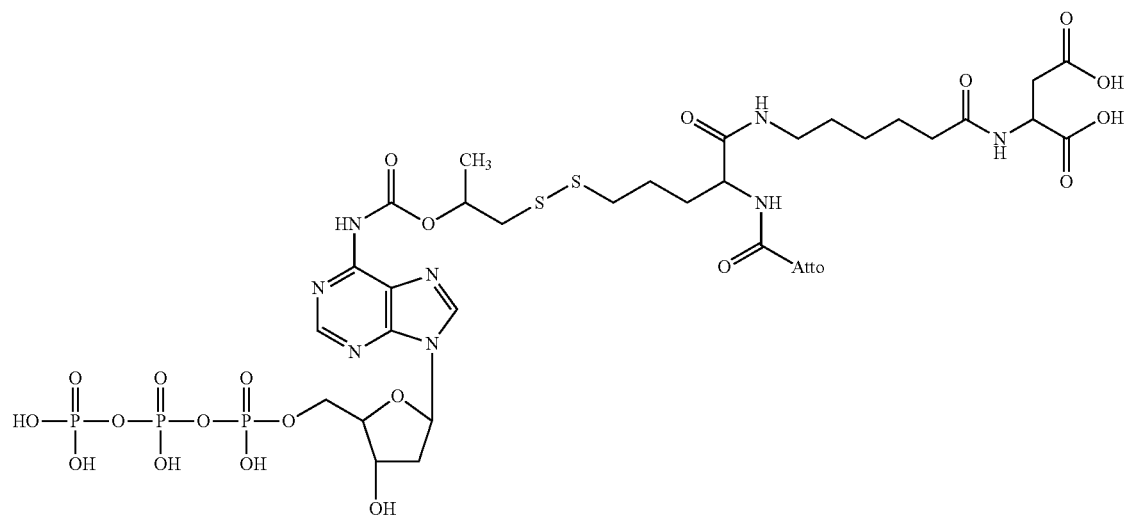
Example 6
Scarless O6 dGTP Synthesis
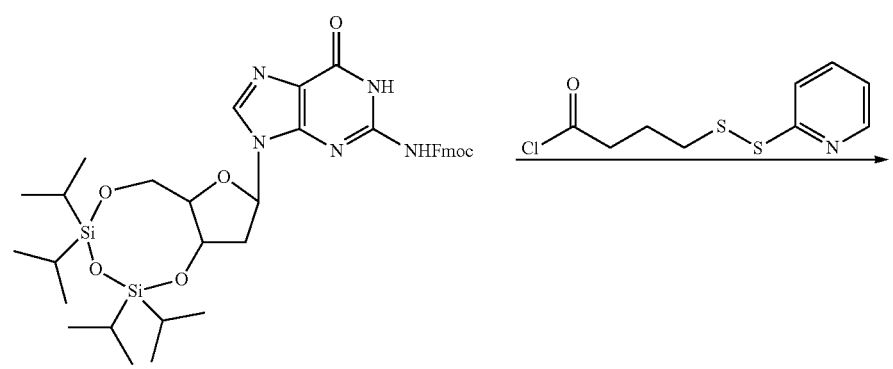

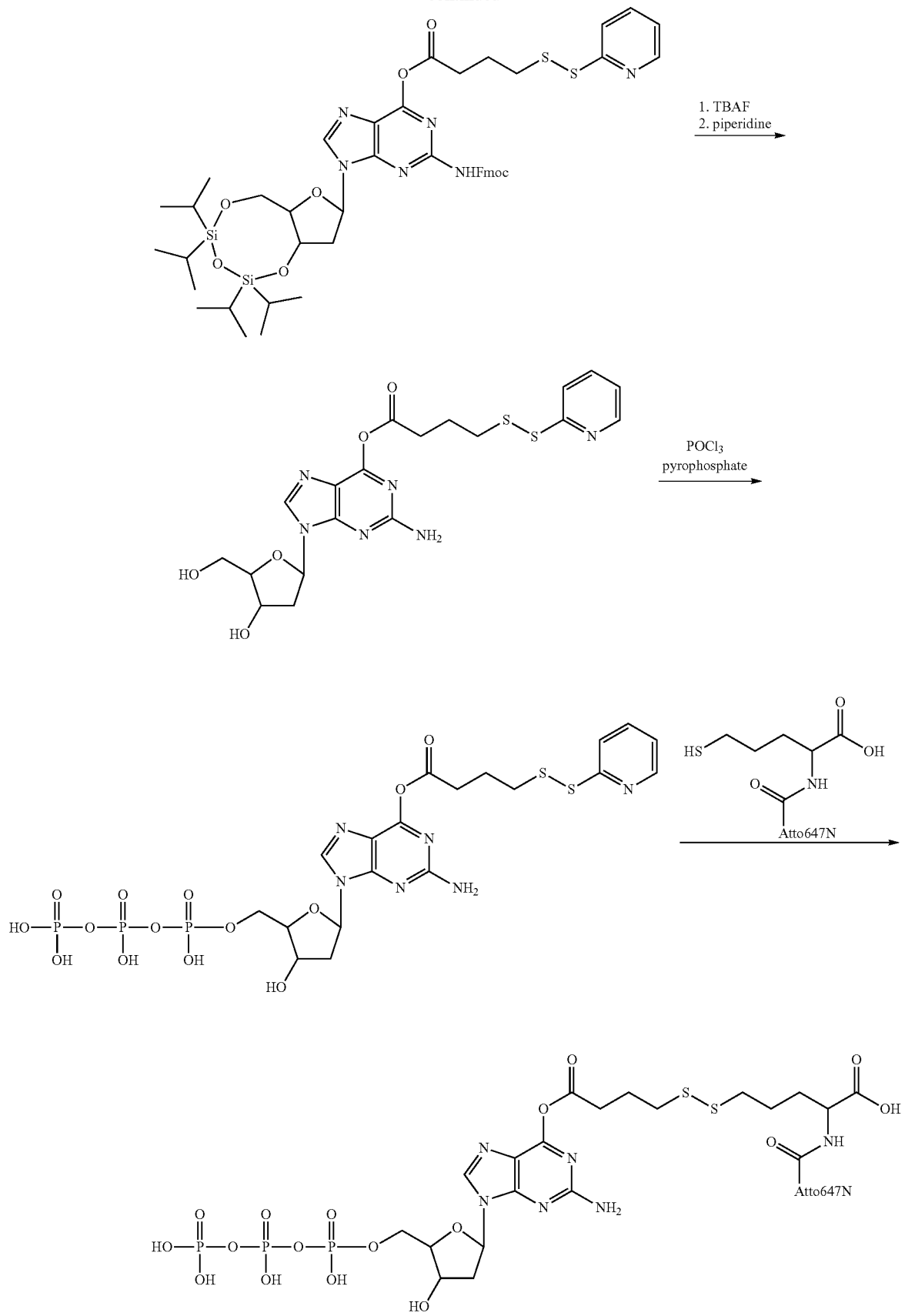

Example 7
Scarless N2 dGTP Synthesis
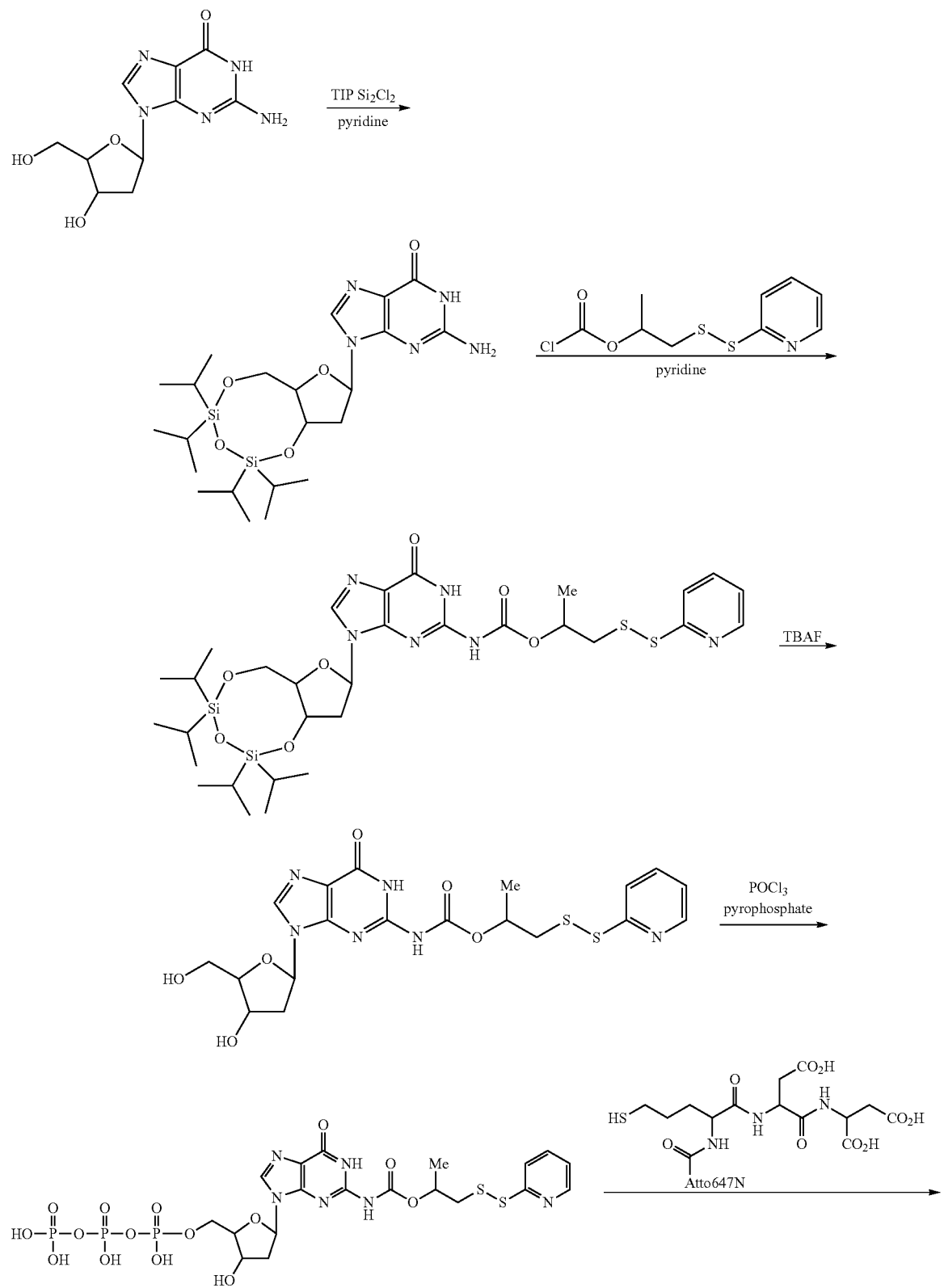

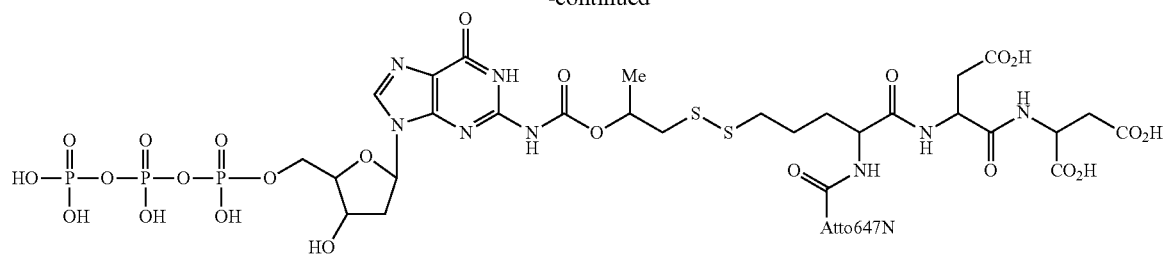
Example 8
Scarless N2 dGTP Synthesis Example
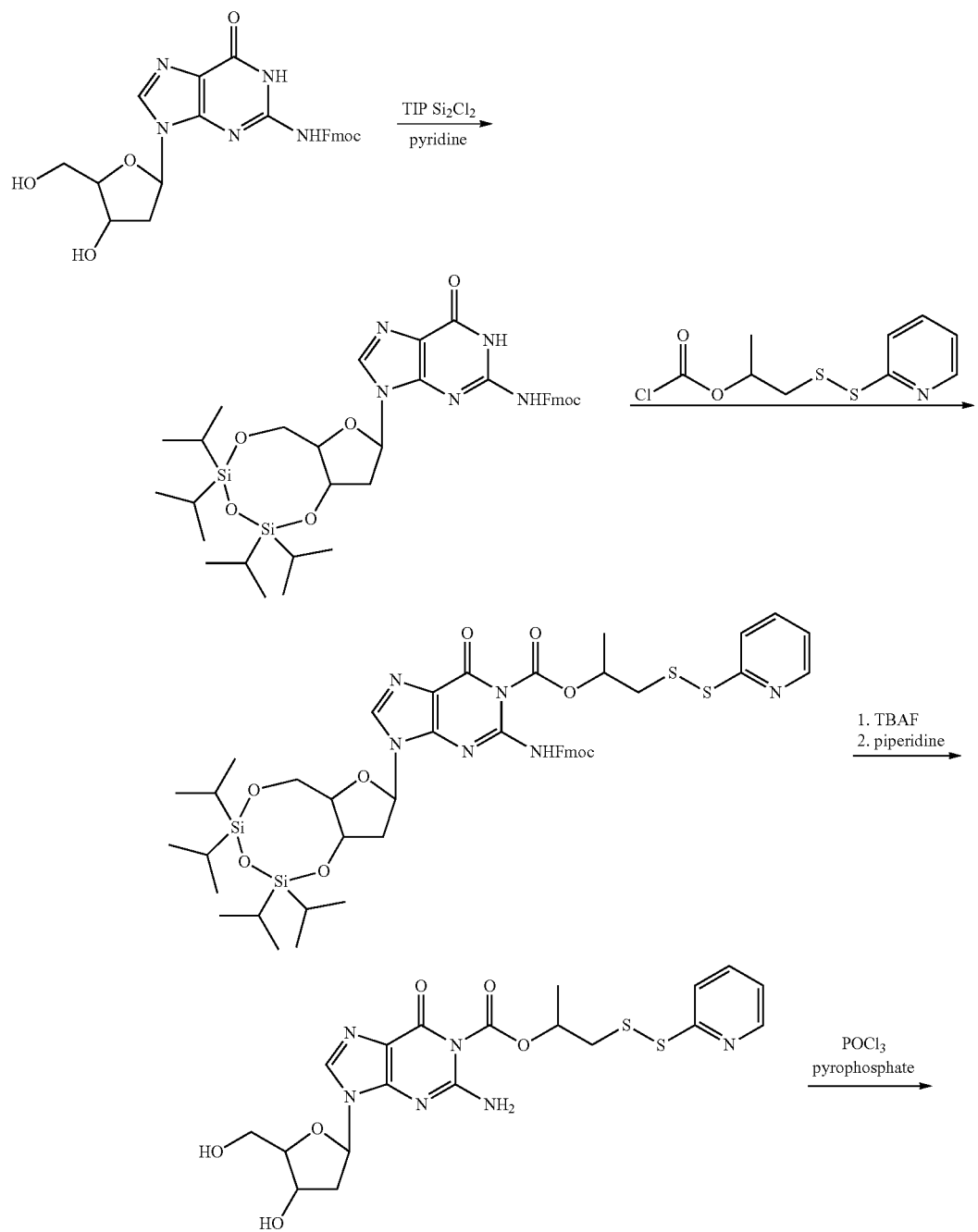

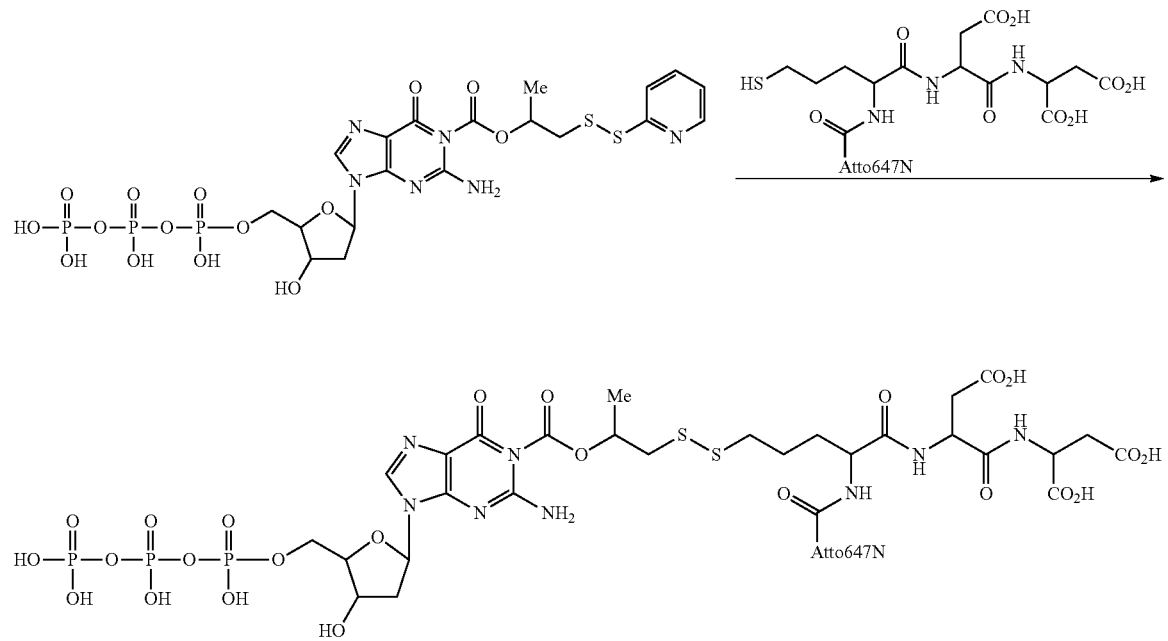
Example 9
Scarless dCTP Synthesis Example
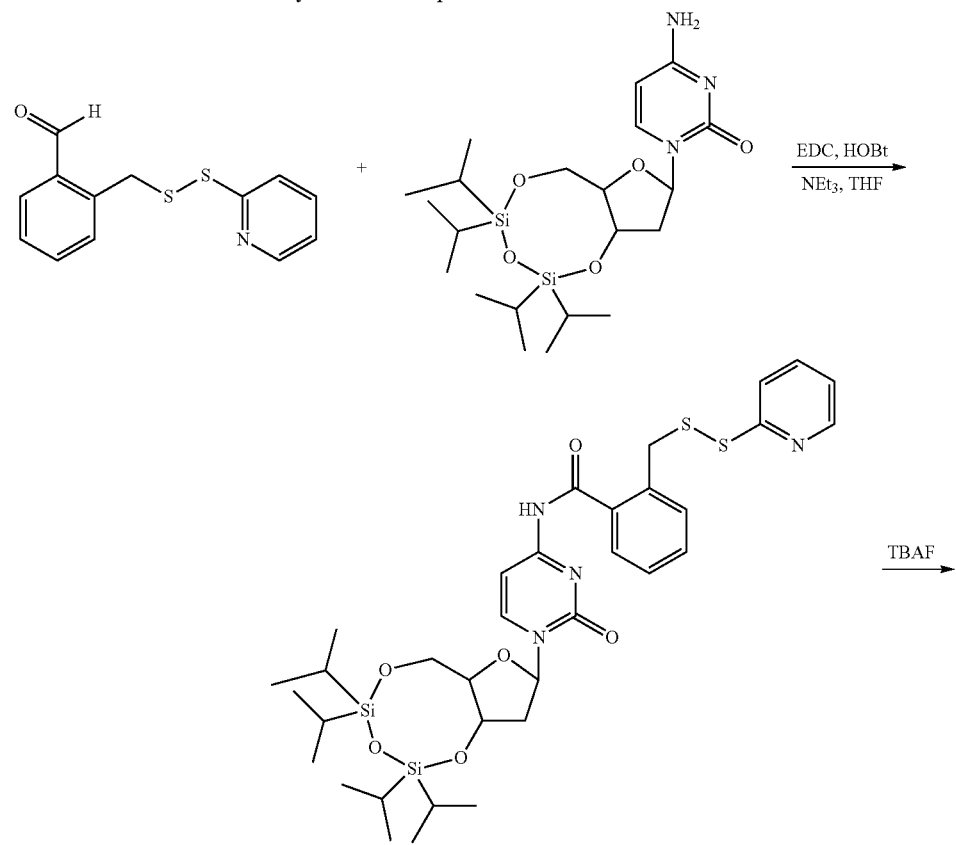

-continued
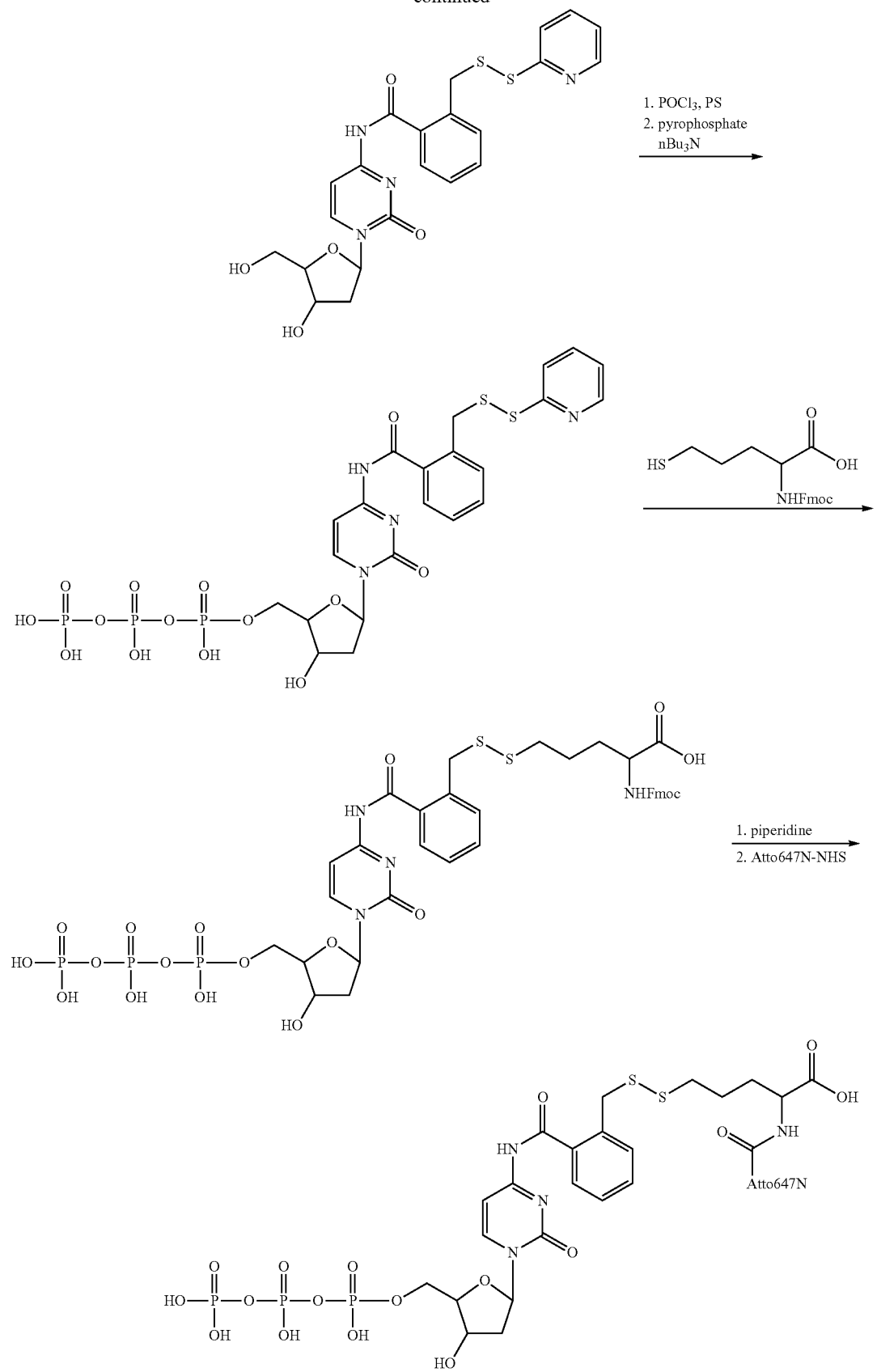

What is claimed is:

1. A nucleotide analog comprising a detectable label attached to the nitrogenous base portion of the nucleotide by a cleavable linker,
   wherein contact of the analog with a reducing agent results in release of the label and elimination of the linker, thereby producing a natural nucleotide, 9-deaza-G, 9-deaza-A, or ψ-uridine, characterized in that no portion of the label or the linker remains attached to the nitrogenous base after cleavage.

2. The analog according to claim 1, wherein the reducing agent is selected from dithiothreitol (DTT), β-mercaptoethanol, dithioerythretol (DTE), GSH, cysteine, cysteamine, tricarboxyethyl phosphine (TCEP), tris(3-hydroxypropyl)phosphine (THPP), glutathione, and salts of sulfurous acid.

3. The analog according to claim 1, wherein the reducing agent is dithiothreitol (DTT).

4. The analog according to claim 1, wherein the reducing agent is tricarboxyethyl phosphine (TCEP).

5. The analog according to claim 1, wherein the linker is a Staudinger linker.

6. The analog according to claim 1, wherein the linker comprises a disulfide bond.

7. The analog according to claim 1, wherein after cleavage of the linker by contact with the reducing agent, a portion of the linker temporarily remains attached to the analog and is thereafter spontaneously eliminated by a cyclization reaction, thereby producing the natural nucleotide, the 9-deaza-G, the 9-deaza-A, or the ψ-uridine.

8. The analog according to claim 1, wherein the linker is attached to the nitrogenous base portion of the analog as follows:
   to N3 of the base when the base is thymine or uracil;
   to N4 of the base when the base is cytosine or adenine;
   to N2 of the base when the base is guanine;
   to N7 of the base when the base is 9-deaza-G or 9-deaza-A; or
   to the N5 when the base is ψ-uridine.

9. The analog according to claim 1, wherein the linker is attached to the nitrogenous base portion of the analog as follows:
   to C5 of the base when the base is thymine, cytosine, or uracil;
   to C7 when the base is adenine or guanine;
   to N7 when the base is 9-deaza-guanine or 9-deaza-adenine; or
   to N5 when the base is ψ-uridine.

10. The analog according to claim 1, wherein the detectable label is a fluorescent label.

11. The analog according to claim 10, wherein the fluorescent label is selected from cyanine, rhodamine, fluorescein, coumarin, BODIPY, alexa, Atto and conjugated multi-dyes.

12. The analog according to claim 1, wherein the detectable label is a non-optically detectable label.

13. A nucleotide analog comprising a structure selected from:

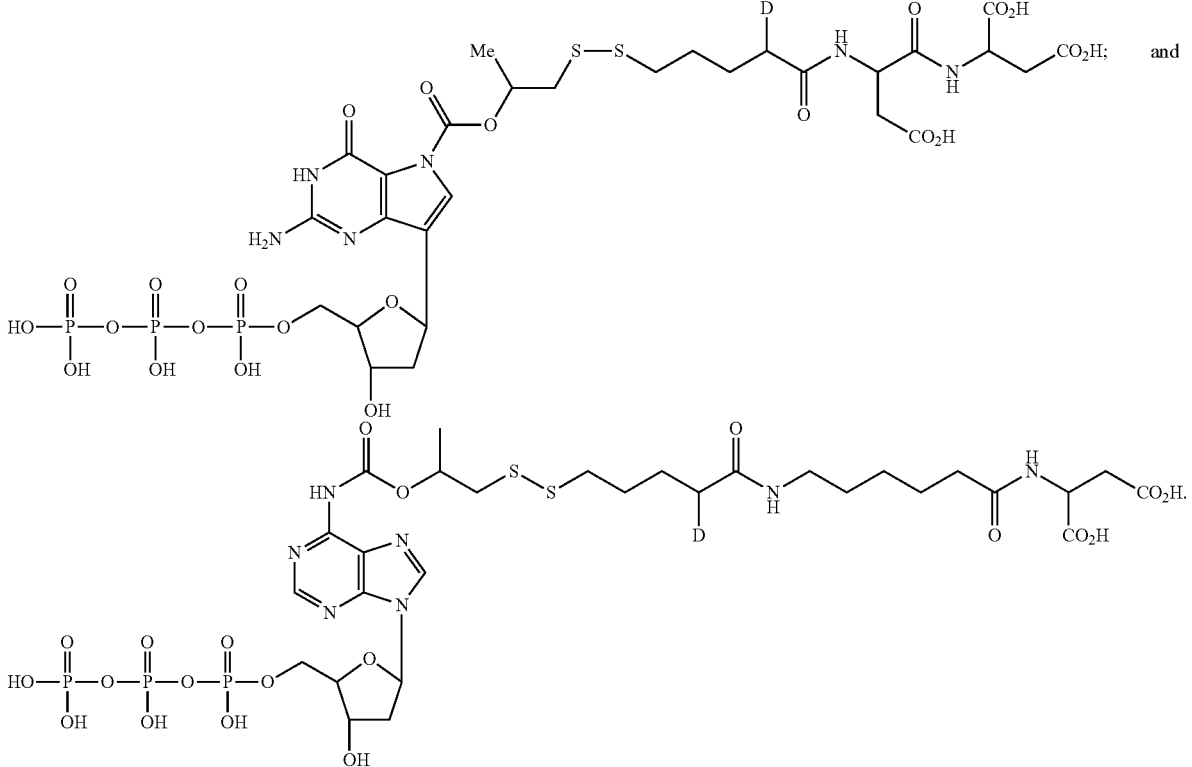

wherein D is a group that comprises a detectable label.

14. A method of sequencing a nucleic acid, the method comprising: directly or indirectly anchoring a nucleic acid duplex to a surface, the duplex comprising a template portion and a primer portion hybridized thereto; exposing the duplex to a nucleotide analog according to claim 1 in the presence of a polymerase capable of catalyzing the addition of the nucleotide analog to the primer portion in a template-dependent manner; detecting incorporation of the nucleotide analog into the primer portion; contacting the nucleic acid duplex with at least one activating agent, thereby cleaving the detectable label and eliminating the linker to produce a natural nucleotide or a 9-deaza-G; and repeating the exposing, detecting, and contacting steps at least once.

15. The method according to claim 14, further comprising: removing unincorporated nucleotide analog and polymerase in all or some repetitions of the exposing, detecting, and contacting steps.

16. The analog according to claim 1, wherein the nitrogenous base is a purine, the linker comprises a disulfide bond (—S—S—), and the linker is attached to the purine through a nitrogen atom in a ring of the purine.

17. The analog according to claim 1, comprising a structure selected from:

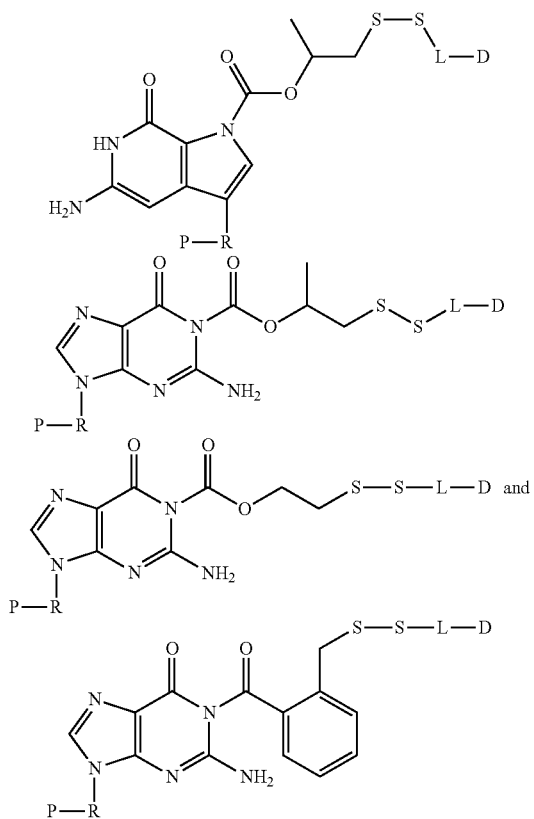

wherein R is a ribose or deoxyribose, P is a mono-, di- or triphosphate, L is a linking component, and D is a group that comprises a detectable label.

18. The analog according to claim 1, wherein the nitrogenous base is a purine, the linker comprises a disulfide bond, and the linker is attached to the purine through a carbon atom in a ring of the purine.

19. The analog according to claim 1, comprising a structure selected from:

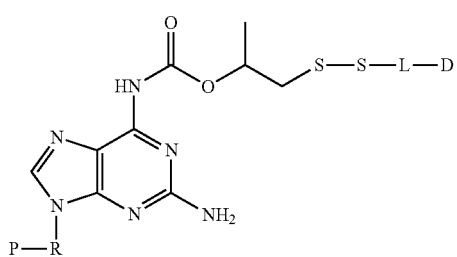

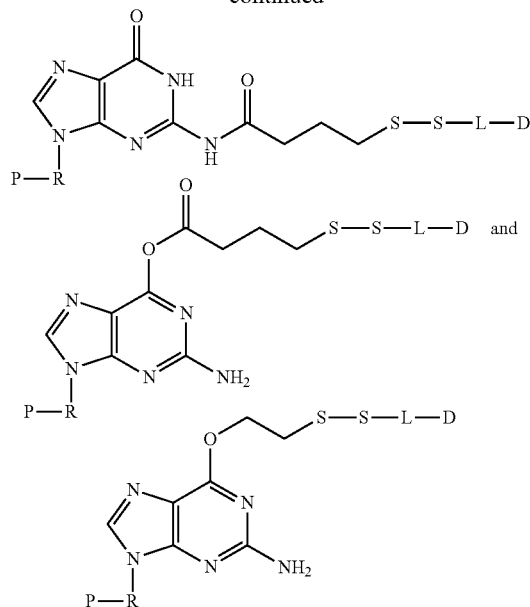

wherein R is a ribose or deoxyribose, P is a mono-, di- or triphosphate, L is a linking component, and D is a group that comprises a detectable label.

20. The analog according to claim 1, wherein the nitrogenous base is a pyrimidine, the linker comprises a disulfide bond, and the linker is attached to the pyrimidine through a nitrogen atom in the ring of the pyrimidine.

21. The analog according to claim 1, comprising a structure selected from:

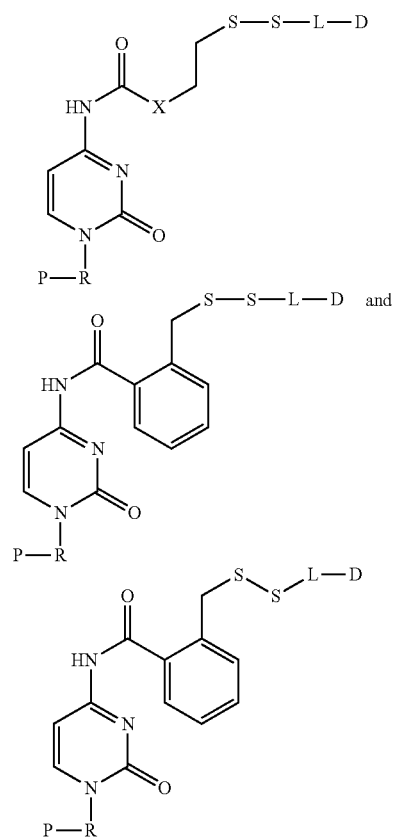

wherein X=O, NH, S, or CH₂, and wherein R is a ribose or deoxyribose, P is a mono-, di- or triphosphate, L is a linking component, and D is a group that comprises a detectable label.

22. The analog according to claim 1, wherein the nitrogenous base is a pyrimidine, the linker comprises a disulfide bond, and the linker is attached to the pyrimidine through a carbon atom in the ring of the pyrimidine.

23. The analog according to claim 1, comprising a structure selected from:

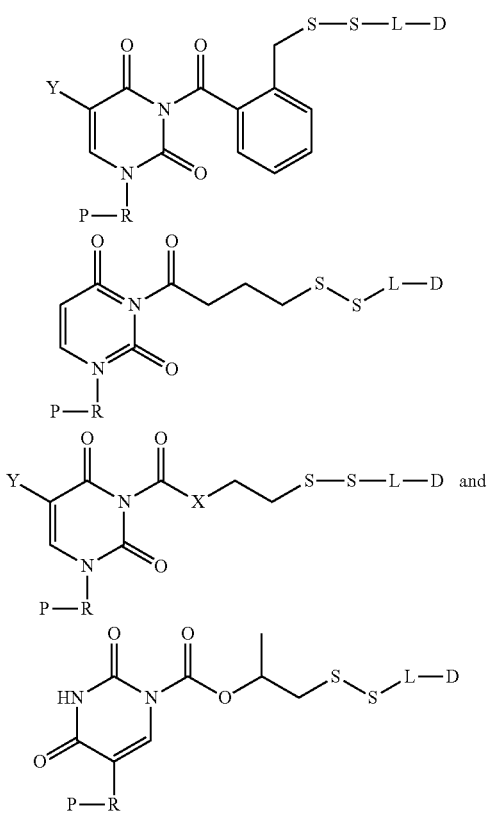

wherein X=O, NH, S, or CH₂; Y=H or CH₃; and wherein R is a ribose or deoxyribose, P is a mono-, di- or triphosphate, L is a linking component, and D is a group that comprises a detectable label.

24. The analog according to claim 1, wherein the linker comprises an azide group (—N₃).

25. The analog according to claim 1, comprising a structure selected from:

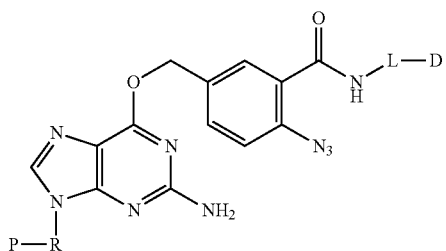

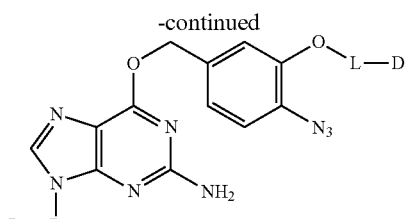

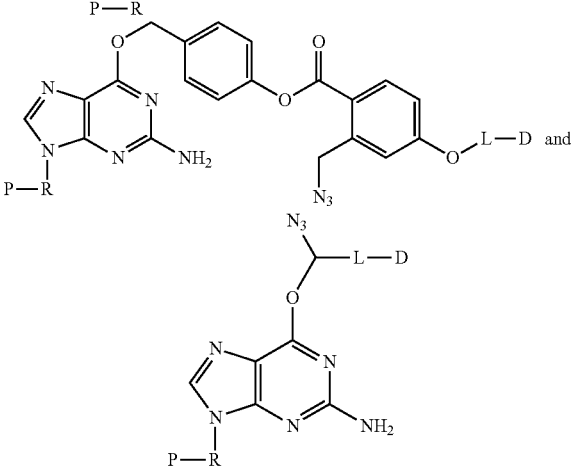

wherein R is a ribose or deoxyribose, P is a mono-, di- or triphosphate, L is a linking component, and D is a group that comprises a detectable label.

26. The analog according to claim 1, wherein the linker comprises a sulfenamide bond (—S—N—).

27. The analog according to claim 1, comprising a structure selected from:

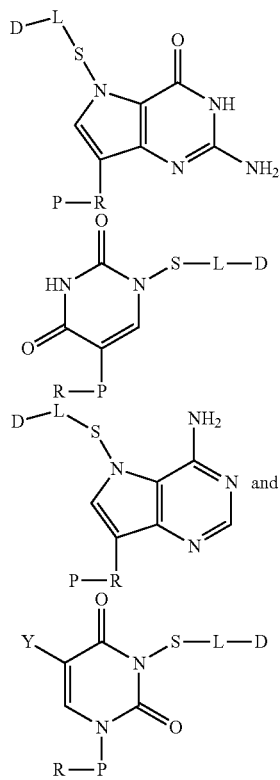

wherein Y=H or CH₃; and wherein R is a ribose or deoxyribose, P is a mono-, di- or triphosphate, L is a linking component, and D is a group that comprises a detectable label.

28. The analog according to claim 1, comprising an inhibitor that is configured so that the analog may be added to a nucleic acid primer by a polymerase, whereupon it inhibits the polymerase from adding a further nucleotide to the primer.

29. The analog according to claim 28, configured so that the inhibitor is released along with the detectable label upon cleavage of the cleavable linker.

30. The analog according to claim 1, wherein the natural nucleotide is adenine, guanine, thymine, cytosine, or uracil.

31. The analog according to claim 1, incorporated into an oligonucleotide.

32. A method of releasing a label from an analog according to claim 1, comprising contacting the analog with a reducing agent, thereby producing a natural nucleotide, 9-deaza-G, 9-deaza-A, or ψ-uridine with no portion of the label or the linker remaining after cleavage.

33. A method of releasing a label from an analog according to claim 31, comprising contacting the oligonucleotide with a reducing agent, thereby producing a natural nucleotide, 9-deaza-G, 9-deaza-A, or ψ-uridine from the analog with no portion of the label or the linker remaining after cleavage.

34. A method of sequencing a nucleic acid, comprising iteratively carrying out the steps of adding a nucleotide analog according to claim 1 in a template-dependent manner to a primer that is duplexed with the nucleic acid, detecting incorporation of the nucleotide analog into the duplex, and then contacting the duplex with a reducing agent, thereby producing a natural nucleotide, 9-deaza-G, 9-deaza-A, ψ-uridine from the added nucleotide analog with no portion of the label or the linker remaining after cleavage.

35. The method of claim 34, wherein the nucleic acid primer duplex is attached to a surface.

36. The method of claim 34, wherein no more than one nucleotide analog is added to the duplex in any single iteration.

37. The analog according to any one of claims 17, 19, 21, 23, 25, and 27, comprising an inhibitor that is configured so that the analog may be added to a nucleic acid primer by a polymerase, whereupon it inhibits the polymerase from adding a further nucleotide to the primer.

38. The analog according to claim 37, configured so that the inhibitor is released along with the detectable label upon cleavage of the cleavable linker.

* * * * *